United States Patent [19]

Tamoto et al.

[11] Patent Number: 5,051,444
[45] Date of Patent: Sep. 24, 1991

[54] PYRROLIDINE DERIVATIVES AS ANTI-AMNESIA AGENTS

[75] Inventors: Katsumi Tamoto; Renzo Ohuchi, both of Toyonaka; Keiichi Ono, Sakai, all of Japan

[73] Assignee: Sumitomo Pharmaceuticals Company, Limited, Osaka, Japan

[21] Appl. No.: 408,562

[22] Filed: Sep. 18, 1989

Related U.S. Application Data

[62] Division of Ser. No. 25,664, Mar. 13, 1987, Pat. No. 4,880,827.

[30] Foreign Application Priority Data

Mar. 18, 1986 [JP] Japan .................. 61-61693
Mar. 20, 1986 [JP] Japan .................. 61-63505

[51] Int. Cl.⁵ .............. A61K 31/415; C07D 207/00; C07D 403/00; C07D 209/02
[52] U.S. Cl. ........................... 514/397; 548/518; 548/540; 548/539; 548/572; 548/336; 548/468; 514/422; 514/423; 514/428; 514/414
[58] Field of Search ............ 548/518, 540, 539, 572, 548/336, 468; 514/422, 423, 428, 397, 414

[56] References Cited

U.S. PATENT DOCUMENTS 4,774,255  9/1988  Black et al. ................ 548/518

FOREIGN PATENT DOCUMENTS 0010347  4/1980  European Pat. Off. ........... 548/518
154353   9/1985  European Pat. Off. ........... 548/518
172458   2/1986  European Pat. Off. ........... 548/518
201741  11/1986  European Pat. Off. ........... 548/518
0201742 11/1986  European Pat. Off. ........... 548/518
0201743 11/1986  European Pat. Off. ........... 548/518
60-172929 9/1985 Japan ........................... 548/518
61-183297 8/1986 Japan ........................... 548/518

OTHER PUBLICATIONS

Science, 211, pp. 601,603 (1981); Weingartner et al.
Brain Research, 157, pp. 414–417 (1978); Bohus, et al.
Journal of Biochemstry, 94 pp. 1179–1190 (1983); Yoshimoto et al.
Biochemistry, 16, pp. 2942–2948 (1977); Yoshimoto et al.
Journal of Neurochemistry, 41, pp. 69–75 (1983); Wilk et al.

Primary Examiner—Mary C. Lee
Assistant Examiner—Robert C. Whittenbaugh
Attorney, Agent, or Firm—Stevens, Davis, Miller & Mosher

[57] ABSTRACT

The present invention relates to pyrrolidine derivatives of the formula

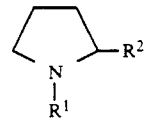

wherein $R^1$ and $R^2$ are defined as herein. The compounds are useful as anti-amnestic agent.

12 Claims, No Drawings

PYRROLIDINE DERIVATIVES AS ANTI-AMNESIA AGENTS

This is a division of application Ser. No. 025,664, filed Mar. 13, 1987, now U.S. Pat. No. 4,880,827.

The present invention relates to pyrrolidine derivatives, and their production and use. More particularly, it relates to pyrrolidine derivatives which have inhibitory action for proline-specific endopeptidase and are useful as anti-amnestic agents.

It is well known that vasopressin plays an important role in the memory process and that the administration of vasopressin exhibits excellent therapeutic effects in the treatment of dementia. [Science, 211, P. 601–603 (1981), Brain Research, 157, P. 414–417 (1978)]

However, vasopressin is easily metabolized in the brain by proline-specific endopeptidase. [Journal of Biochemistry, 94, p. 1179–1190 (1983)].

Thus, the inhibitor of proline-specific endopeptidase is expected to increase the content of vasopressin in the brain and to be useful for the treatment of dementia.

It is reported about proline-specific endopeptidase inhibitory agents, for instance N-benzyloxycarbonylglycyl-L-prolylchloromethane and N-benzyloxycarbonyl-L-prolylprolinal [Biochemistry, 16, P. 2942–2948 (1977), Journal of Neurochemistry, 41, P. 69–75 (1983)]. In addition it is known that such proline-specific endopeptidase inhibitors are useful for anti-amnestic agent [Japan Koukai 60-172929, 60-188317, 61-37764, 61-183297, 61-238775, 61-238776, 61-238799.]

We have been studying many kinds of pyrrolidine derivatives and found that pyrrolidine derivatives of the invention have excellent inhibitory activity of proline-specific endopeptidase and also have strong effects on the model of assay of the anti-amnestic action.

Said pyrrolidine derivatives are represented by the formula:

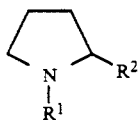

(I)

wherein $R^1$ is

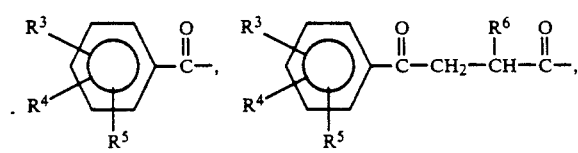

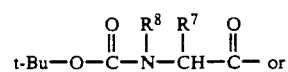

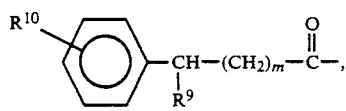

$R^2$ is

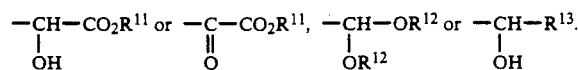

$R^3$, $R^4$, and $R^5$ are each independently hydrogen or hydroxy group or halogen or lower alkyl, phenyl, substituted phenyl, $-CH_2R^{14}$, $-X-R^{15}$,

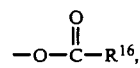

$-NH_2$, $-NHR^{17}$ or

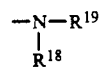

(in which $R^{14}$ is phenyl or substituted phenyl. X is oxygen atom or sulfur atom. $R^{15}$ is lower alkyl, phenyl, substituted phenyl or $-CH_2R^{20}$ (in which $R^{20}$ is phenyl or substituted phenyl) $R^{16}$ is lower alkyl, phenyl, substituted phenyl or $-CH_2R^{21}$ (in which $R^{21}$ is phenyl or substituted phenyl). $R^{17}$ is lower alkyl, five or six-membered cycloalkyl, phenyl, substituted phenyl, $-CH_2R^{22}$ (in which $R^{22}$ is phenyl or substituted phenyl) or

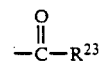

in which $R^{23}$ is lower alkyl or phenyl or substituted phenyl). $R^{18}$ and $R^{19}$ are each independently lower alkyl or $-CH_2R^{24}$ (in which $R^{24}$ is phenyl, substituted phenyl)). $R^6$ is hydrogen or lower alkyl. $R^7$ is hydrogen, lower alkyl, benzyl,

or $-(CH_2)_n-R^{25}$ (in which n is an integer of 0 to 4. $R^{25}$ is $-OH$, $-SH$, $-NH_2$, $-SCH_3$,

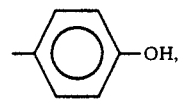

$-CONH_2$,

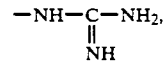

heterocyclic group, or $-CO_2R^{26}$ (in which $R^{26}$ is hydrogen, lower alkyl or benzyl)). $R^8$ is hydrogen or, when $R^8$ and $R^7$ are taken together with the adjacent nitrogen atom and carbon atom to which they are attached, they represent five-membered heterocyclic group. $R^9$ is hydrogen, lower alkyl, phenyl or substituted phenyl. $R^{10}$ is hydrogen, lower alkyl, lower alkoxy or halogen. m is an integer of 0 to 3. $R^{11}$ is hydrogen, lower alkyl, phenyl, substituted phenyl or $-CH_2R^{27}$ (in which $R^{27}$ is phenyl or substituted phenyl). $R^{12}$ is lower alkyl or, when $R^{12}$ and $R^{12}$ are each taken together, they represent lower alkylene. $R^{13}$ is lower alkyl, phenyl, substituted phenyl or —CH$_2$R$^{28}$ (in which R$^{28}$ is phenyl or substituted phenyl).

Among the above-mentioned compounds, examples of preferable ones are compounds wherein R$^1$ is

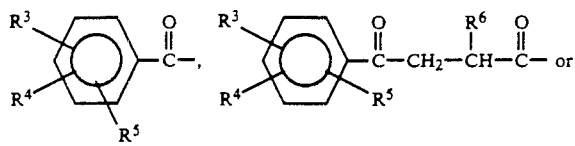

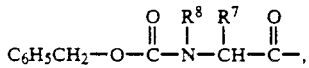

and R$^2$ is

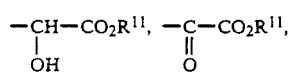

(R$^{11}$ is lower alkyl)

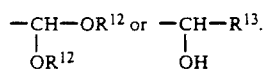

Examples of more preferable ones are compounds wherein R$^1$ is

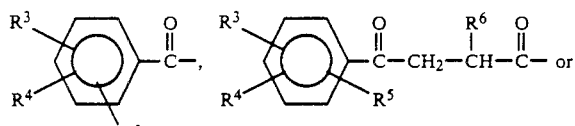

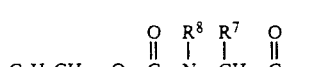

and R$^2$ is

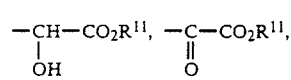

(R$^{11}$ is lower alkyl).

Examples of furthermore preferable ones are compounds wherein R$^1$ is

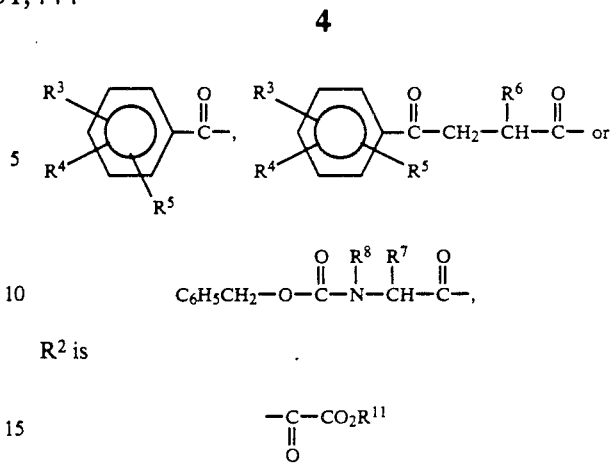

R$^2$ is $$-\underset{\underset{O}{\|}}{C}-CO_2R^{11}$$

(R$^{11}$ is lower alkyl).

In the significances as defined above, the term "substituted phenyl" means phenyl having halogen, lower alkyl or lower alkoxy. The term "halogen" includes fluorine, chlorine, bromine, and iodine. The term "lower alkoxy" is intended to means a straight or branched chain alkoxy group having 1 to 4 carbon atoms (e.g. methoxy, ethoxy, n-propoxy, isopropoxy, n-butoxy, sec-butoxy etc.). The term "lower alkyl" is intended to mean a straight or branched chain alkyl group having 1 to 4 carbon atoms (e.g. methyl, ethyl, n-propyl, isopropyl, n-butyl, sec-butyl etc.). The term "lower alkylene" means a straight chain alkylene group having 2 to 3 carbon atoms (e.g. ethylene, triethylene). The term "heterocyclic group" includes mono- or bicyclic heterocyclic group having at least one of nitrogen atom and 3-8 carbon atoms (e.g. imidazole, indole etc.). Five-membered heterocyclic group represent pyrrolidine etc.

Pyrrolidine derivatives (I) inhibit the action of proline-specific endopeptidase which is thought to be main metabolic enzymes for vasopressin and show an excellent effect on the model of assay of the anti-amnestic action.

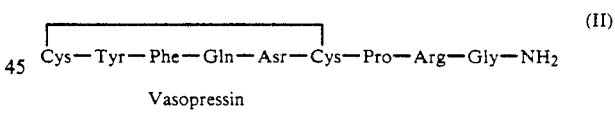

Vasopressin

According to the present invention, the pyrrolidine derivatives (I) are obtainable, for instance, by the following synthetic route.

(1) The first route

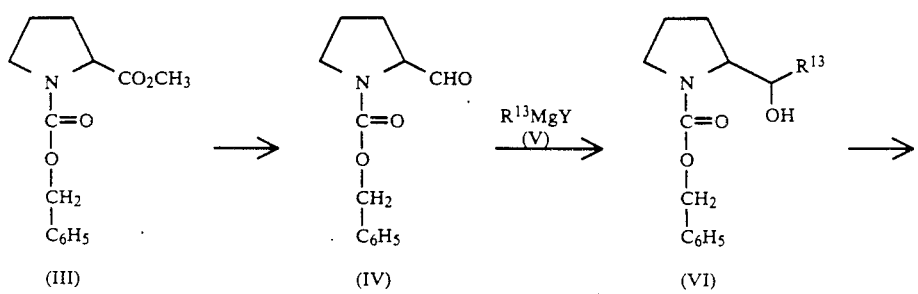

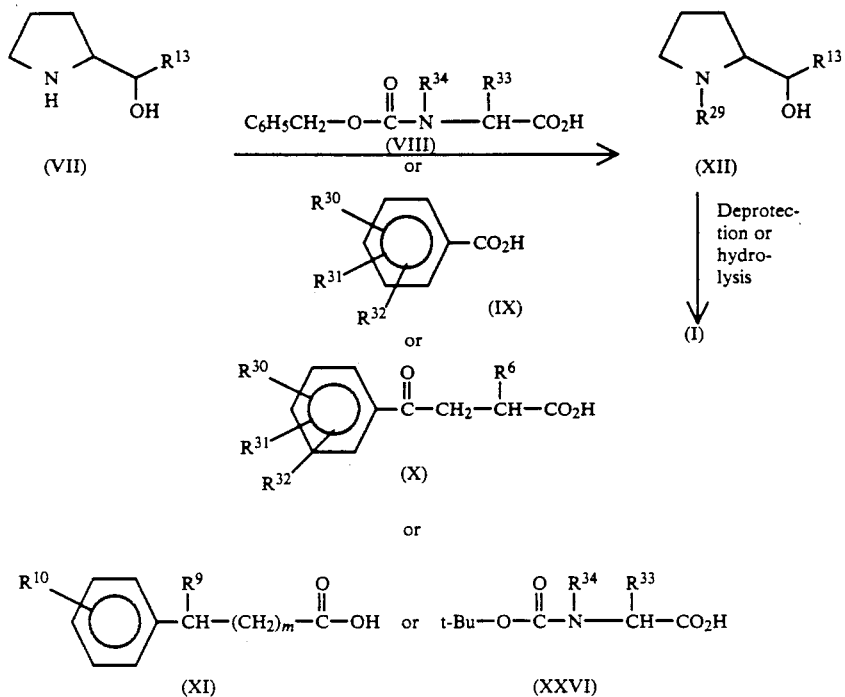

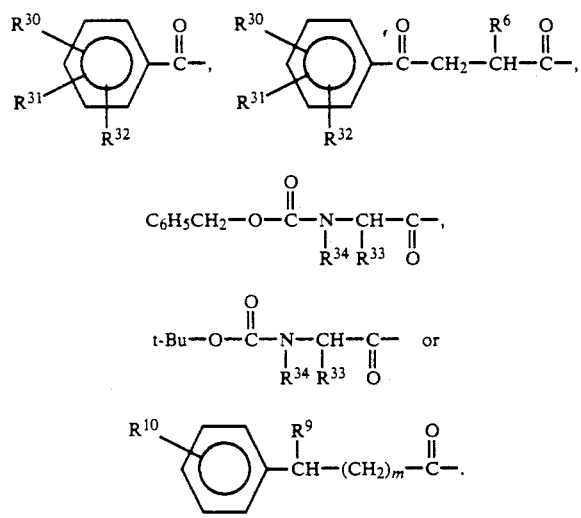

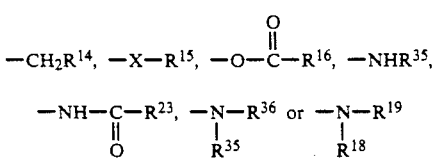

Wherein $R^6$, $R^9$, $R^{10}$, m, and $R^{13}$ are each as defined above. Y is chlorine, bromine or iodine. $R^{29}$ is

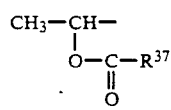

$R^{30}$, $R^{31}$, and $R^{32}$ are each independently hydrogen, halogen, hydroxy group, lower alkyl, phenyl, substituted pnenyl,

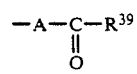

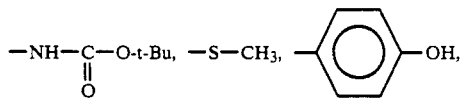

in which X, $R^{14}$, $R^{15}$, $R^{16}$, $R^{18}$, $R^{19}$, and $R^{23}$ are each as defined above. $R^{35}$ is $$\text{t-Bu}-O-\underset{\underset{O}{\|}}{C}- \text{ or } C_6H_5CH_2-O-\underset{\underset{O}{\|}}{C}-.$$

$R^{36}$ is lower alkyl, five or six-membered cycloalkyl, phenyl, substituted phenyl or —$CH_2R^{22}$ (in which $R^{22}$ is as defined above.). $R^{33}$ is hydrogen, lower alkyl, Benzyl, $$\begin{array}{c} CH_3-CH- \\ | \\ O-C-R^{37} \\ \| \\ O \end{array}$$

or —$(CH_2)_n$-$R^{38}$. (in which $R^{37}$ is lower alkyl, benzyl or phenyl. n is as defined above. $R^{38}$ is $$-A-\underset{\underset{O}{\|}}{C}-R^{39}$$

(in which $R^{39}$ is lower alkyl, benzyl or phenyl. A is oxygen atom or sulfur atom), $$-NH-\underset{\underset{O}{\|}}{C}-O\text{-t-Bu}, \quad -S-CH_3, \quad \phantom{X}\!\!\!\!\!\!\!\bigcirc\!\!\!\!\!\!\!\phantom{X}-OH,$$

$$-CONH_2, \quad -NH-\underset{\underset{NH_2\cdot HZ'}{|}}{\overset{\overset{NH}{\|}}{C}}-NH_2\cdot HZ'$$

(in which Z' is chlorine or bromine), —$CO_2R^{40}$ (in which $R^{40}$ is lower alkyl or benzyl) or heterocyclic group). $R^{34}$ is hydrogen or, when $R^{34}$ and $R^{33}$ are taken together with adjacent nitrogen atom and carbon atom which they are attached, they represent five-membered heterocyclic group. A synthetic method of aldehyde compound (IV) production is known. [A. Ito et al Chem. Pharm. Bull., 23, P.3081-3087 (1975)]. The conversion of the compound (IV) into compound (VI) can be acomplished by the reaction of the former with a Grignard reagent of the formula: $R^{13}MgY$ (V) in ethers (e.g. ethyl ether, tetrahydrofuran etc.) at a temperature ranging from room temperature to 50° C. Grignard reagent can be prepared by general method. Deprotection of the compound (VI) can be carried out using a catalyst (e.g. 5% Pd-c) for hydrogenolysis in alcohols (e.g. methanol, ethanol, etc.) at room temperature and atmospheric pressure or using excess thioanisol in trifluoroacetic acid [Y. Kiso et al Peptido Chemistry, P.193 (1979)].

The compound (XII) can be obtainable by reacting the compound (VII) with carboxylic acids (e.g. compound (VIII) or (IX) or (X) or (XI) or (XXVI)) in the presence of condensing a agent and reaction stimulator. If necessary, tertiary amine (triethylamine) may be added. An example of the condensing agent is dicyclohexylcarbodiimide or 1-ethyl -3-(3-dimethylaminopropyl)carbodiimide hydrochloride (hereinafter this compound is abbreviated to WSC) etc. The reaction stimulator is 1-hydroxybenzotriazole (hereinafter this compound is abbreviated to HOBt), N-hydroxy-5-norbornen-2,3-dicarboxyimide (hereinafter this compound is abbreviated to HONB) or N-hydroxysucciimide (hereinafter this compound is abbreviated to HOSu) etc. The reaction solvent is ethers (e.g. tetrahydrofuran etc.), halogenated hydrocarbons (e.g. chloroform or dichloromethane etc.) N,N-dimethylformamide etc. The reaction is conducted at a preferable temperature from −20° C. to room temperature.

When there is possibility of racemization in the condensation reactions, it is preferable that the reaction is conducted at low temperature (e.g. −10° C.-−20° C.) in the beginning early of the reaction and the reaction mixture is warmed slowly to room temperature.

The subsequent deprotection or hydrolysis of the compound (XII) to the compound (I) can be carried out by a per se conventional procedure.

(2) The Secone Route

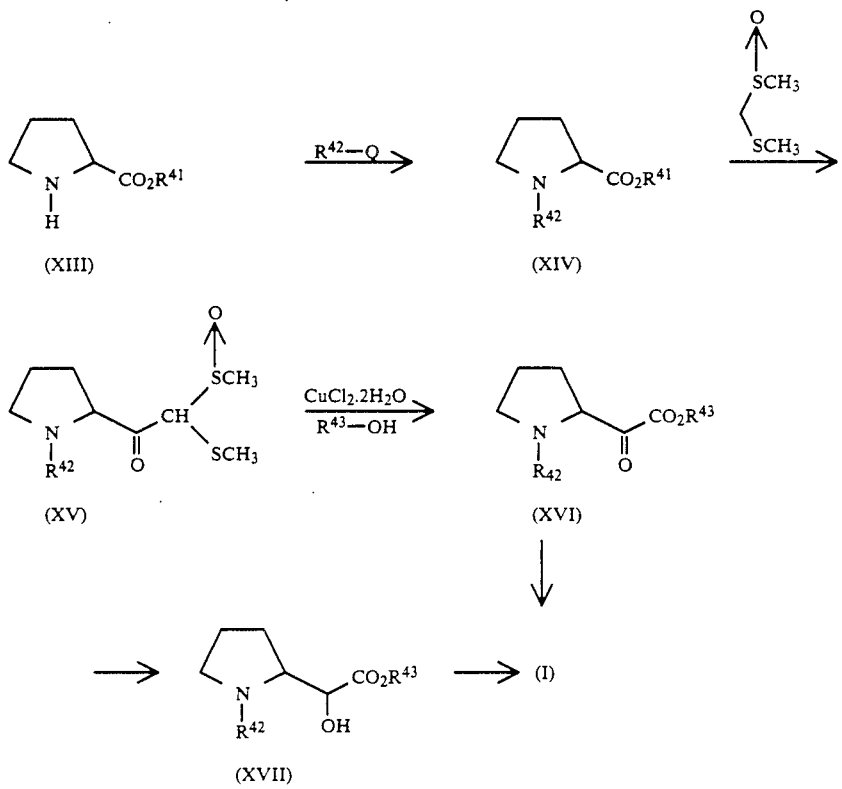

Wherein $R^{41}$ is lower alkyl or benzyl. Q is hydroxy group or chlorine or bromine.

$R^{42}$ is 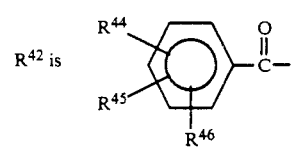

(in which $R^{44}$, $R^{45}$, and $R^{46}$ are each independently hydrogen, lower alkyl, lower alkoxy or halogen). $R^{43}$ is lower alkyl.

The compound (XIV) can be obtained by reacting the compound (XIII) with acid halide ($R^{42}$-Cl or $R^{42}$-Br) under ice-cooling in an inert solvent. It is preferable to use an acid-accepting agent such as an organic or inorganic base (e.g. alkali hydroxide, alkali carbonate, tertiary-amine, etc.) in the reaction. The inert solvent is water or ethers (e.g. tetrahydrofuran etc.). Of course the compound (XIV) can be obtainable by reacting the compound (XIII) with carboxylic acid ($R^{42}$-OH) in the presence of condensing agent (e.g. WSC etc.) and reaction stimulator (e.g. HOBt etc.) in the same manner as in the first route.

The compound (XV) can be obtained by reacting compound (XIV) with methyl methylsulfinylmethyl sulfide in the presence of the base in an inert solvent at a temperature ranging from −20° C. to room temperature. The example of the base is alkali metal hydride or alkali metal t-butoxide. The inert solvent is ethers (e.g. 1,2-dimethoxyethane, tetrahydrofuran etc.). Generally the base and methyl methylsulfinylmethyl sulfide are used more than twice molar of the compound (XIV). The conversion of the compound (XV) into the compound (XVI) can be accomplished by using cupric chloride dihydrate or cupric chloride anhydrous in alcohols (e.g. methanol, ethanol etc.). The amount of cupric chloride used is equivalent to or more in moles to that of the compound (XV). Reduction of the compound (XVI) is carried out using sodium borohydride in alcohols (e.g. methanol, ethanol etc.) at a temperature ranging from $-20°$ C. to room temperature.

(3) THE THIRD ROUTE

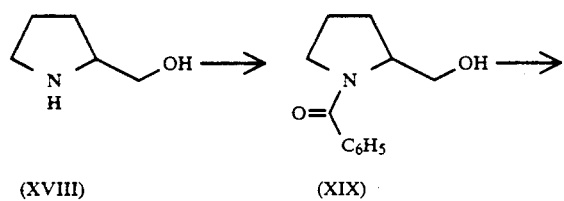

(XVIII)　　　　　　(XIX)

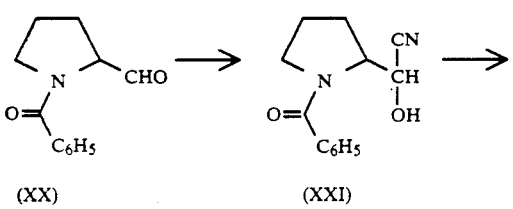

(XX)　　　　　　(XXI)

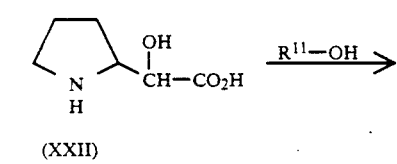

(XXII)

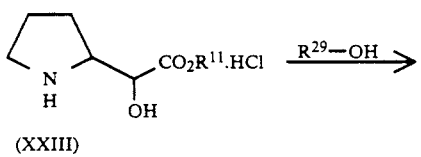

(XXIII)

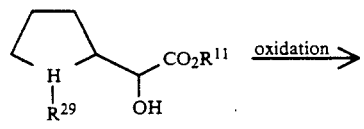

(XXIV)

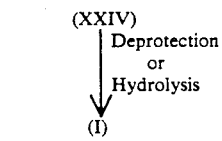

(I)

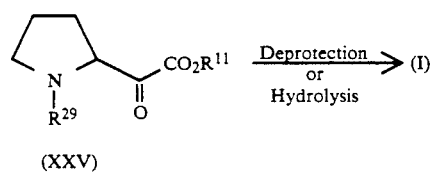

(XXV)

(in which $R^{11}$ and $R^{29}$ are each as defined above).

Compounds (XIX), (XX), (XXI), and (XXII) are prepared in the same manner as the procedure described in Japan Kokai 54-61151.

Esterification of the compound (XXII) can be conducted by reacting the compound (XXII) with alcohols ($R^{11}$-OH: e.g. ethanol, methanol etc.) in the presence of thionyl chloride at a temperature ranging from $-10°$ C. to $-20°$ C.

The compound (XXIV) is prepared in the same manner as the procedure described in the first route.

The oxidation is carried out in the same manner as the procedure described in [Synthesis 165-185 (1981)]. For example the oxidation is conducted using dimethylsulfoxide (hereinafter this compound is abbreviated to DMSO), base (e.g. triethylamine etc.), and oxalyl chloride or trifluoroacetic acid anhydride. When the reaction is carried out using DMSO, triethylamine and oxalyl chloride in an inert solvent, a temperature ranging from $-60° \sim -50°$ C. is favorable. The inert solvent is dichloromethane etc. Oxalyl chloride needs to be used more than twice molar of the compound (XXIV). The subsequent deprotection or hydrolysis of the compound (XXIV) or (XXV) to the compound (I) can be carried out by a per se conventional procedure.

(4) THE FOURTH ROUTE

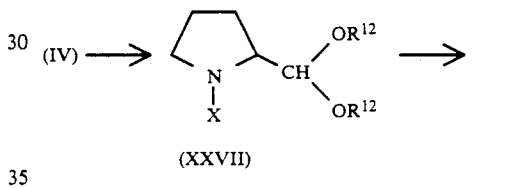

(XXVII)

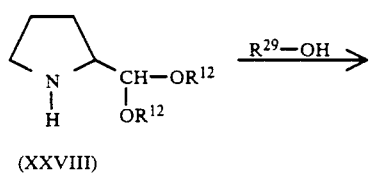

(XXVIII)

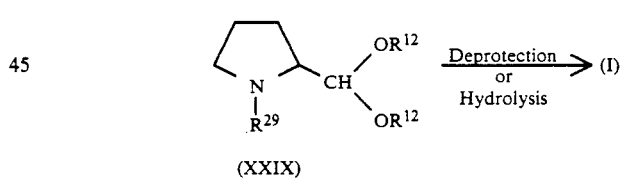

(XXIX)

Wherein Z is

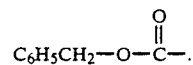

$R^{12}$ and $R^{29}$ are each as defined above.

The conversion of the compound (IV) into the compound (XXVII) can be accomplished by using orthoformates (e.g. triethyl orthoformate trimethyl orthoformate etc.), p-toluenesulfonic acid and alcohols (e.g. methanol, ethanol, ethylene glycol etc.). The compound (XXVIII) or (XXIX) is prepared in the same manner as in the first route. The subsequent deprotection or hydrolysis of the compound (XXIX) to the compound (I) may be carried out by a per se conventional procedure for deprotection or hydrolysis as occasion demands.

The pyrrolidine derivatives (I) as well as their acid addition salts can be administered orally or parenterally in the form of conventional pharmaceutical preparations. For instance, they can be administered orally in the form of conventional solid pharmaceutical preparations such as tablets, capsules, syrups and suspensions. Alternatively, they can be administered parenterally by injection in the form of conventional liquid pharmaceutical preparations such as solutions, emulsions, suspensions, etc. Also, they may be directly applied to the rectum in the form of a suppository. Further, the preparations may contain physiologically acceptable carriers, excipients, activators, binding agents, stabilizers, etc. In the case of injections, physiologically acceptable buffers, solubilizing agents or isotonic agents may be incorporated therein. The daily dosage may vary depending upon the symptoms of disease, the age and body weight of the patient, the administration route, etc., and the normal dosage to a human adult is between 1 mg and 1000 mg, preferably between 5 mg and 500 mg dividing in one to several times per day.

Following compounds are obtainable by the present inventions.

1. L-1-(L-N-benzyloxycarbonylvalyl)-2-{(S)-1-hydroxyethyl}pyrrolidine

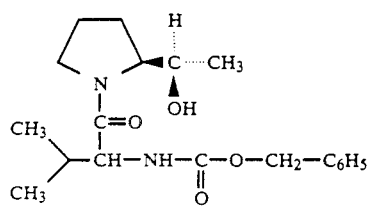

2. L-1-(L-N-benzyloxycarbonylvalyl)-2-{(R)-1-hydroxyethyl}pyrrodidine

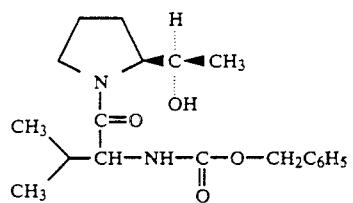

3. L-1-(L-N-benzyloxycarbonylvalyl)-2-{(S)-1-hydroxy-n-propyl}pyrrolidine

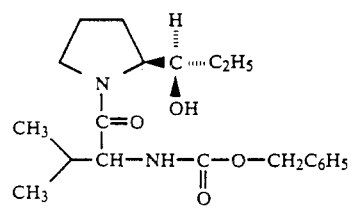

4. L-1-(L-N-benzyloxycarbonylvalyl)-2-{(R)-1-hydroxy-n-propyl}pyrrolidine

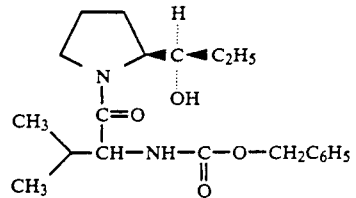

5. L-1-(L-N-benzyloxycarbonylvalyl)-2-{(S)-1-hydroxy-2-methylpropyl}pyrrolidine
6. L-1-(L-N-benzyloxycarbonylvalyl)-2-{(R)-1-hydroxy-2-methylpropyl}pyrrolidine
7. L-1-(L-N-benzyloxycarbonylvalyl)-2-{(R,S)-1-hydroxy-n-butyl}pyrrolidine
8. L-1-(L-N-benzyloxycarbonylvalyl)-2-{(R,S)-1-hydroxy-1-phenylmethyl}pyrrolidine
9. L-1benzoyl-2-{(R,S)-1-hydroxy-n-propyl}pyrrolidine

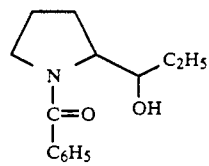

10. L-1-(3-benzoylpropionyl)-2-{(R,S)-1-hydroxy-n-propyl}pyrrolidine

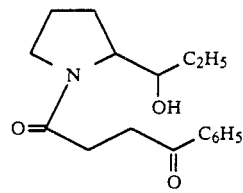

11. L-1-(L-N-benzyloxycarbonylprolyl)-2-{(R,S)-1-hydroxy-n-propyl}pyrrolidine

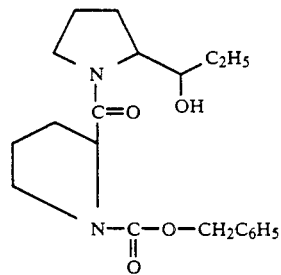

12. L-1-(L-N-benzyloxycarbonylisoleucyl)-2-{(R,S)-1-hydroxy-n-propyl}pyrrolidine

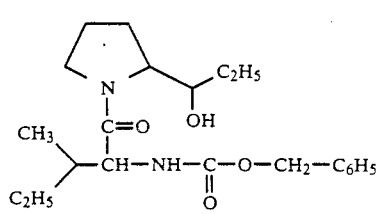

13. L-1-(L-N-benzyloxycarbonylphenylalanyl)-2-{(R,S)-1-hydroxy-n-propyl}pyrrolidine
14. L-1-(3-benzoylpropionyl)-2-{(R)-1-hydroxy-2-methylpropyl}pyrrolidine
15. L-1-(3-benzoylpropionyl)-2-{(S)-1-hydroxy-2-methylpropyl}pyrrolidine
16. L-1-(3-benzoylpropionyl)-2-{(R,S)-1-hydroxy-n-butyl}pyrrolidine
17. L-1-(3-benzoylpropionyl)-2-{(R)-1-hydroxy-1-phynylmethyl}pyrrolidine
18. L-1-(3-benzoylpropionyl)-2-{(S)-1-hydroxy-1-phenylmethyl}pyrrolidine
19. Ethyl (R,S)-2-hydroxy-2-(L-1-benzoylpyrrolidin-2-yl)acetate

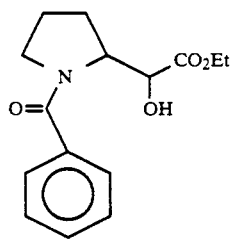

20. Ethyl 2-oxo-2-(L-1-benzoylpyrrolidin-2-yl)acetate

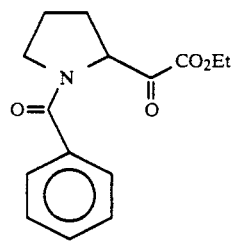

21. Ethyl (R,S)-2-hydroxy-2-{L-1-(3-benzoylpropionyl)-pyrrolidin-2-yl}acetate

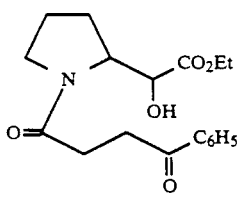

22. Ethyl 2-oxo-2-{L-1-(3-benzoylpropionyl)pyrrolidin-2-yl}acetate

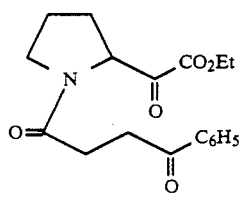

23. Ethyl (R,S)-2-hydroxy-2-{L-1-(L-N-benzyloxycarbonylvalyl)pyrrolidin-2-yl}acetate

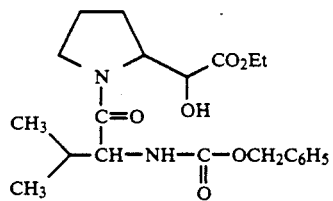

24. Ethyl 2-oxo-2-{L-1-(L-N-benzyloxycarbonylvalyl)-pyrrolidin-2-yl}acetate

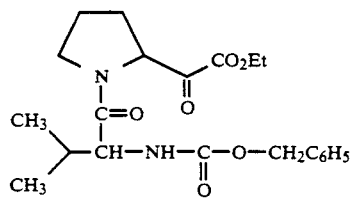

25. Ethyl (R,S)-2-hydroxy-2-{L-1-(L-N-benzyloxycarbonylisoleucyl)pyrrolidin-2-yl}acetate

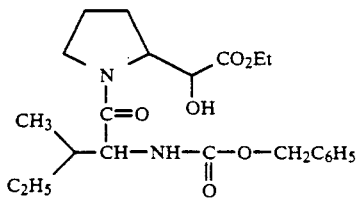

26. Ethyl 2-oxo-2-{L-1-(L-N-benzyloxycarbonylisoleucyl)pyrrolidin-2-yl}acetate

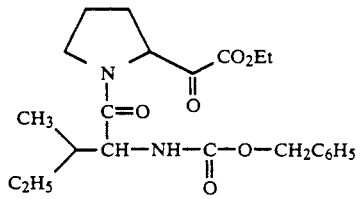

27. Ethyl (R,S)-2-hydroxy-2-{L-1-(L-N-benzyloxycarbonylpropyl)pyrrolidin-2-yl}acetate

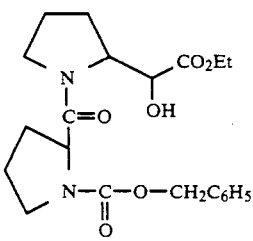

28. Ethyl 2-oxo-2-{L-1-(L-N-benzyloxycarbonylprolyl)pyrrolidin-2-yl}acetate

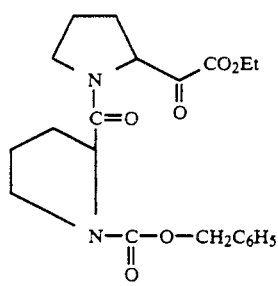

29. L-1-(L-N-benzyloxycarbonylvalyl)-2-(1,3-dioxolan-2-yl)pyrrolidine

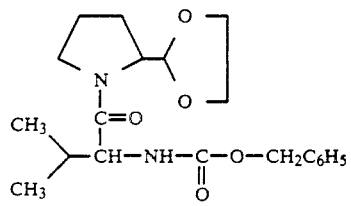

30. L-1-(L-N-benzyloxycarbonylprolyl)-2-(1,3-dioxolan-2-yl)pyrrolidine

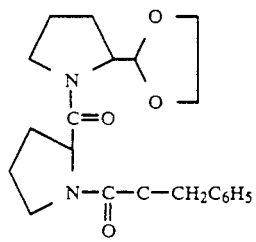

31. Ethyl (R,S)-2-hydroxy-2-{L-1-(4-methoxybenzoyl)-pyrrolidin-2-yl}acetate

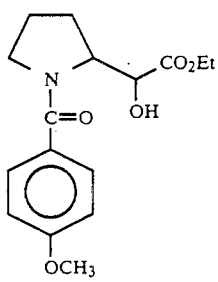

32. Ethyl 2-oxo-2-{L-1-(4-methoxybenzoyl)pyrrolidin-2-yl}acetate

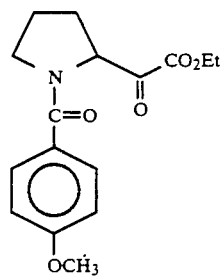

33. Ethyl (R,S)-2-hydroxy-2-{L-1-(4-hydroxybenzoyl)-pyrrolidin-2-yl}acetate

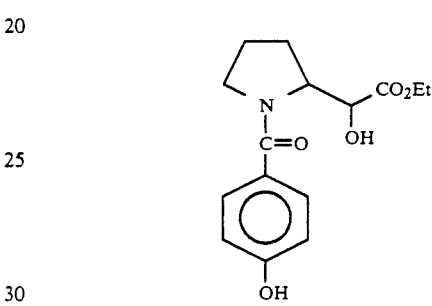

34. Ethyl 2-oxo-2-{L-1(4-hydroxybenzoyl)pyrrolidin-2-yl}acetate

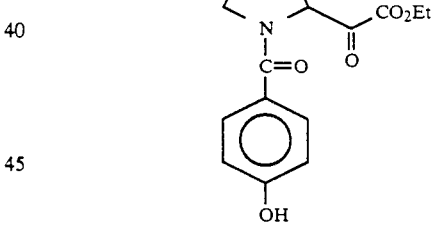

35. Ethyl (R,S -2-hydroxy-2-{L-1-(4-methylbenzoyl)-pyrrolidin-2-yl}acetate

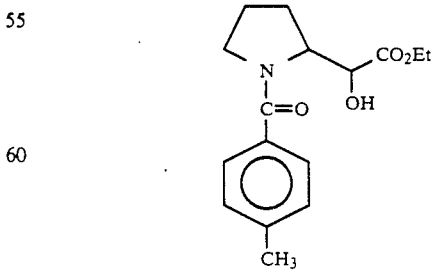

36. Ethyl 2-oxo-2-{L-1-(4-methylbenzoyl)pyrrolidin-2-yl}acetate

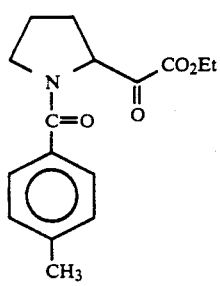

37. Ethyl (R,S)-2-hydroxy-2-{L-1-(4-fluorobenzoyl)-pyrrolidin-2-yl}acetate

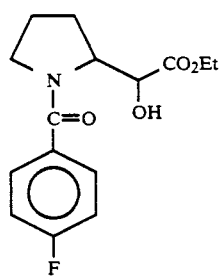

38. Ethyl 2-oxo-2-{L-1-(4-fluorobenzoyl)pyrrolidin-2-yl}acetate

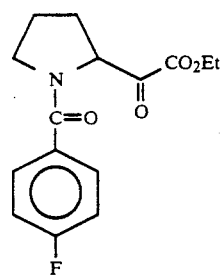

39. Ethyl (R,S)-2-hydroxy-2-{L-1-(3,4-dimethoxybenzoyl)pyrrolidin-2-yl}acetate

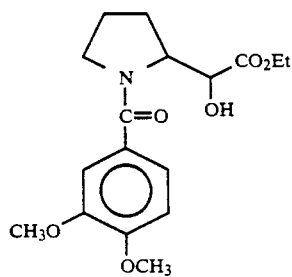

40. Ethyl 2-oxo-2-{L-1-(3,4-dimethoxybenzoyl)pyrrolidin-2-yl}acetate

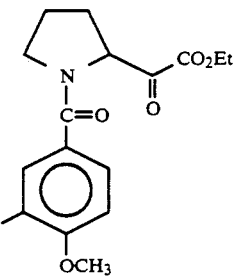

41. Ethyl (R,S)-2-hydroxy-2-{L-1-(3,4,5-trimethoxybenzoyl)pyrrolidin-2-yl}acetate

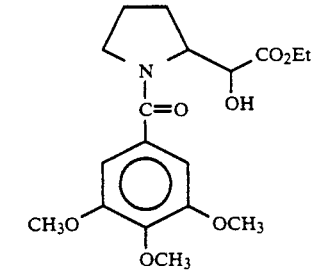

42. Ethyl 2-oxo-2-{L-1-(3,4,5-trimethoxybenzoyl)pyrrolidin-2-yl}acetate

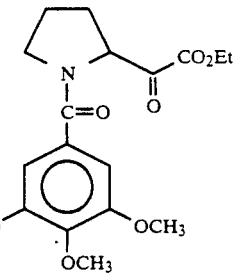

43. Ethyl (R,S)-2-hydroxy-2-[L-1-{3-(4-n-butoxybenzoyl)propionyl}pyrrolidin-2-yl]acetate

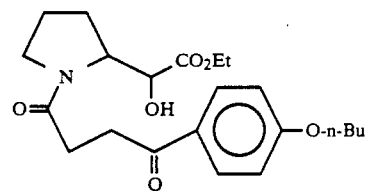

44. Ethyl 2-oxo-2-[L-1-{3-(4-n-butoxybenzoyl)propionyl}pyrrolidin-2-yl]acetate

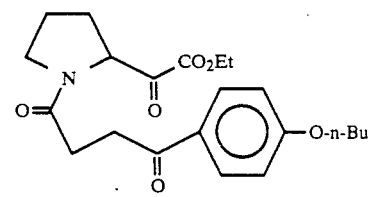

45. Ethyl (R,S)-2-hydroxy-2-[L-1-{3-(4-t-butylbenzoyl)propionyl}pyrrolidin-2-yl]acetate

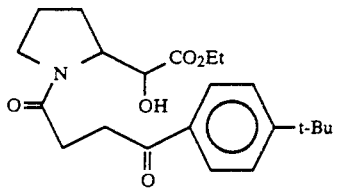

46. Ethyl 2-oxo-2-[L-1-{3-(4-t-butylbenzoyl)propionyl}pyrrolidin-2-yl]acetate

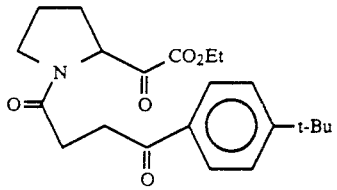

47. Ethyl (R,S)-2-hydroxy-2-{L-1-(4-benzyloxybenzoyl)pyrrolidin-2-yl}acetate

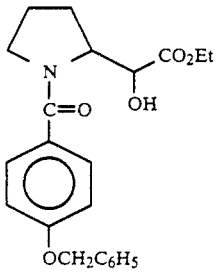

48. Ethyl 2-oxo-2-{L-1-(4-benzyloxybenzoyl)pyrrolidin2-yl}acetate

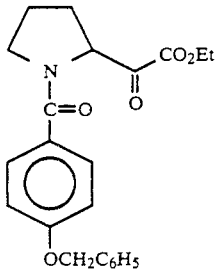

49. Ethyl (R,S)-2-hydroxy-2-[L-1-{3-(2,5-dimethoxybenzoyl) propionyl}pyrrolidin-2-yl]acetate

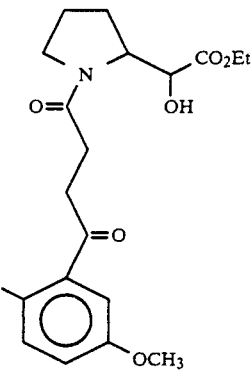

50. Ethyl 2-oxo-2-[L-1-{3-(2,5-dimethoxybenzoyl) propionylpyrrolidin-2-yl}acetate

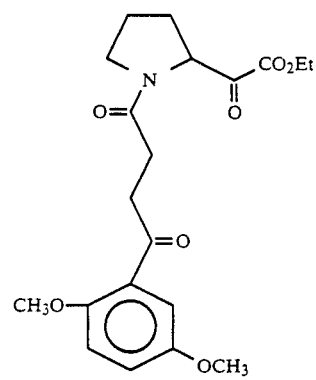

Practical and presently preferred embodiments of the invention are illustratively shown in the following Reference Examples or Examples, which are not intended to limit the scope of the invention thereto.

REFERENCE EXAMPLE 1

Preparation of L-1-benzyloxycarbonyl-2-{(R,S)-1-hydroxyethyl}pyrrolidine

Magnesium (0.2 g, 8.6 mmol) and iodine (catalytic amount) were added to ether (10 ml). To this suspension was added dropwise an ether (3 ml) solution of methyl iodide (1.8 g, 12.7 mmol) at the rate of gently reflux under a nitrogen atomosphere. After 20 minutes an ether (10 ml) solution of L-N-benzyloxycarbonyl-2-formylpyrrolidine (2.0 g, 8.6 mmol) was added dropwise to the reaction mixture, followed by stirring for 2 hours. A cold saturated aqueous ammonium chloride solution was added dropwise to the reaction mixture with ice-cooling. The mixture was extracted with ether. The extract was washed with a saturated aqueous sodium chloride solution and dried over anhydrous magnesium sulfate. Evaporation of the solvent gave an oil, which was subjected to column chromatography on silica gel. Elution with n-hexane: ethyl acetate=1:1 gave two products which have different $R_f$ value each other. The NMR spectra data of the two products were showed. One product has higher $R_f$ value, L-1-benzyloxycarbonyl-2-{(R) or (S)-1-hydroxyethyl}pyrrolidine NMR(CDCl$_3$)δ: 1.13 (3H, d, J=8 Hz), 1.50–2.30 (4H, m), 3.20–4.20 (4H, m), 5.10 (2H, S), 7.33 (5H, S)

The other product which has lower $R_f$ value, L-1-benzyloxycarbonyyl-2-{(S) or (R)-1-hydroxyethyl}pyrrolidine
NMR(CDCl$_3$)δ: 1.17 (3H, d, J=5 Hz), 1.50–2.20 (4H, m), 3.20–4.20 (4H, m), 5.10 (2H, S), 7.32 (5H, S)

The following compounds were prepared in the same manner as in Reference Example 1. The NMR spectra data of the compounds were described.

(a)
L-1-Benzyloxycarbonyl-2-{(R,S)-1-hydroxy-n-propyl}pyrrolidine
NMR(CDCl$_3$)δ: 0.96 (3H, t, J=7 Hz), 1.20–2.20 (6H, m), 3.10–4.10 (4H, m), 4.60 (1H, S), 5.10 (2H, S), 7.30 (5H, S)

(b)
L-1-Benzyloxycarbonyl-2-{(R,S)-1-hydroxy-n-butyl}pyrrolidine
NMR(CDCl$_3$)δ: 0.80–2.30 (11H, m), 3.20–4.10 (4H, m), 5.10 (2H, S), 7.30 (5H, S)

(c)-1
L-1-Benzyloxycarbonyl-2-{(R) or (S)-1-hydroxy-2-methylpropyl}pyrrolidine (this compound has higher $R_f$ value in the two products)
NMR(CDCl$_3$)δ: 0.90 (3H, d, J=6 Hz), 1.00 (3H, d, J=6 Hz), 1.50–2.20 (4H, m), 3.20–4.30 (5H, m), 5.10 (2H, S), 7.33 (5H, S)

(c)-2
L-1-Benzyloxycarbonyl-2-{(S) or (R)-1-hydroxy-2-methylpropyl}pyrrolidine (this compound has lower $R_f$ value in the two products)
NMR(CDCl$_3$)δ: 0.90 (3H, d, J=6 Hz), 1.00 (3H, d, J=6 Hz), 1.50–2.50 (4H, m), 3.20 4.50 (4H, m), 5.17 (2H, S), 7.34 (5H, S)

(d)
L-1-Benzyloxycarbonyl-2-{(R,S)-1-hydroxy-1-pheylmethyl}pyrrolidine
NMR(CDCl$_3$)δ: 1.30–2.20 (4H, m), 3.00–3.80 2H, m), 4.00–4.50 (1H, m), 4.50–4.80 (1H, m), 5.20 (2H, S), 7.10–7.60 (10H, m)

REFERENCE EXAMPLE 2

Preparation of L-2-{(R) or (S)-1-hydroxyethyl}pyrrolidine

L-1-Benzyloxycarbonyl-2-{(R) or (S)-1-hydroxyethyl}pyrrolidine (1.2 g, 4.9 mmol) (this compound was obtained in the Reference Example 1 and has higher $R_f$ valure in the two products) and thioanisole (24.3 g, 196.0 mmol) was added to trifluoroacetic acid (70 ml), followed by stirring for 2 hours at room temperature. After removal of trifluoroacetic acid by distillation under the reduced pressure, benzene (100 ml) was added to the residue. Benzene was evaporated under reduced pressure, the residue was shaked with n-hexane (100 ml) and n-hexane layer was removed. This operation was repeated 3 times, and title compound was obtained.

REFERENCE EXAMPLE 3

Preparation of L-2-{(S) or (R)-1-hydroxyethyl}-pyrrolidine

L-1-Benzyloxycarboxyl-2-{(S) or (R)-1-hydroxyethyl}pyrrolidine (1.2 g, 4.9 mmol) (this compound was obtained in Reference Example 1 and has lower $R_f$ value in the two products) and thioanisole (24.3 g, 196 mmol) were reacted in trifluoroacetic acid (70 ml) in the same manner as in Reference Example 2, there was obtained L-2-{(S) or (R)-1-hydroxyethyl}pyrrolidine.

REFERENCE EXAMPLE 4

Preparation of L-2-{(R,S)-1-hydroxy-n-propyl}pyrrolidine

5% Pd-C (1.5 g) was added to a methanol (30 ml) solution of L-1-benzyloxycarbonyl-2-{(R,S)-1-hydroxy-n-propyl}pyrrolidine (1.5 g, 5.7 mmol). Hydrogenolysis is carried out at room temperature and atmospheric pressure.

REFERENCE EXAMPLE 5

Preparation of L-2-{(R) or (S)-1-hydroxy-2-methylpropyl}pyrrolidine

In the same manner as in Reference Example 4 but using L-1-benzyloxycarbonyl-2-{(R) or (S)-1-hydroxy-2-methylpropyl}pyrrolidine (this compound was obtained in Reference Example 1-(C)-1) as the starting materials, there was obtained L-2-{(R) or (S)-1-hydroxy-2-methylpropyl}pyrrolidine.

REFERENCE EXAMPLE 6

Preparation of L-2-{(S) or (R)-1-hydroxy-2-methylpropyl}pyrrolidine

In the same manner as in Reference Example 4 but using L-1-benzyloxycarbonyl-2-{(S) or (R)-1-hydroxy-2-methylpropyl}pyrrolidine (this compound was obtained in Reference Example 1-(C)-2) as the starting materials, there was obtained L-2-{(R) or (S)-1-hydroxy-2-methylpropyl}pyrrolidine.

REFERENCE EXAMPLE 7

Preparation of L-2-{(R,S)-1-hydroxy-n-butyl}pyrrolidine

In the same manner as in Reference Example 4 but using L-1-benzyloxycarbonyl-2-{(R,S)-1-hydroxy-n-butyl}pyrrolidine as the starting materials, there was obtained L-2-{(R,S)-1-hydroxy-n-butyl}pyrrolidine.

REFERENCE EXAMPLE 8

Preparation of L-2-{(R,S)-1-hydroxy-1-phenylmethyl}pyrrolidine

In the same manner as in Reference Example 4 but using L-1-benzyloxycarbonyl-2-{(R,S)-1-hydroxy-1-phenylmethyl}pyrrolidine as the starting materials, there was obtained L-2-{(R,S)-1-hydroxy-1-phenylmethyl}pyrrolidine.

REFERENCE EXAMPLE 9

Preparation of methyl L-1-benzoylprolinate

Methyl L-prolinate hydrogen chloride (10.0 g, 60 mmol) was added to an aqueous sodium hydrogen carbonate (11 g) solution. Benzoyl chloride (8.5 g, 60 mmol) was added dropwise to the reaction mixture with ice-cooling, followed by stirring for five hours. The reaction mixture was extracted with ethyl acetate. The extract was dried over anhydrous magnesium sulfate. Evaporation of ethyl acetate gave methyl L-1-benzoylprolinate.
NMR(DMSO-d$_6$)δ: 1.70–2.50 (4H, m), 3.20–3.90 (5H, m), 4.20–4.63 (1H, m), 7.43 (5H, s)

REFERENCE EXAMPLE 10

Preparation of ethyl (R,S)-2-hydroxy-2-(L-pyrrolidin-2-yl)acetate hydrochloride

Thionyl chloride (0.78 g, 6.6 mmol) was added dropwise to ethanol below −15° C. (R,S)-2-Hydroxy-2-(L-pyrrolidin-2-yl)acetic acid (0.95 g, 6.6 mmol) was added to the reaction mixture, followed by stirring for 30 minutes below −15° C. and overnight at room temperature. Evaporation of ethanol gave ethyl (R,S)-2-hydroxy-2-(L-pyrrolidin-2-yl)acetate hydrochloride.
NMR(CD$_3$OD-CDCl$_3$)δ: 1.30 (3H, t, J=7 Hz), 1.70-2.50 (4H, m), 3.20-3.60 (2H, m), 3.65-4.60 (4H, m).

REFERENCE EXAMPLE 11

Preparation of L-1-benzyloxycarbonyl-2-(1,3-dioxolan-2-yl)pyrrolidine

A benzene (100 ml) solution of L-1-benzyloxycarbonyl-2-formylpyrrolidine (4.7 g), triethyl orthoformate, and p-toluenesulfonic acid (0.5 g) was heated under reflux for 0.5 hr. When the reaction was carried out, the flask was attached to a water separator. The reaction mixture was poured into an aqueous sodium hydrogen carbonate solution and extracted with benzene. The extract was washed with water, dried over anhydrous magnesium sulfate. Evaporation of benzene gave L-1-benzoylcarbonyl-2-(1,3-dioxolan-2-yl)pyrrolidine.
NMR(CDCl$_3$)δ: 1.60-2.20 (4H, m), 3.30-4.40 (8H, m), 5.15 (2H, s), 7.37 (5H, s).

REFERENCE EXAMPLE 12

Preparation of L-(1,3-dioxolan-2-yl)pyrrolidine

In the same manner as in Reference Example 4 but using L-1-benzyloxycarbonyl-2-(1,3-dioxolan-2-yl)pyrrolidin as the starting materials, there was obtained L-(1,3-dioxolan-2-yl)pyrrolidine.

EXAMPLE 1

Preparation of L-1-(L-N-benzyloxycarbonylvalyl)-2-{(R) or (S)-1-hydroxy-n-propyl}pyrrolidine HOBt (0.8 g, 5.9 mmol) and L-N-benzyloxyvaline (1.45 g, 5.9 mmol) was added to chloroform (50 ml) and cooled to −10° C.~−20° C. To this mixture were added L-2-{(R,S)-1-hydroxy-n-propyl}pyrrolidine (0.82 g, 5.9 mmol), triethylamine (1 ml), and WSC (1.1 g, 5.9 mmol), followed by stirring for 2 hours at −10° C.~−20° C. and overnight at room temperature. Water was added to the reaction mixture, the mixture was extracted with chloroform. The extract was washed successively with an aqueous sodium hydrogen carbonate solution and a saturated aqueous sodium chloride solution, dried over anhydrous magnesium sulfate. Evaporation of the solvent gave an oil, which was subjected to column chromatography on silica gel. The column was developed with 0.5 l of n-hexane: ethyl acetate=2:1 and successively with 0.5 l of n-hexane: ethyl acetate=1:1. Elution with ethyl acetate gave two products which have different R$_f$ value each other.
The NMR spectra data of the two products were showed.

One product which has higher R$_f$ value, L-1-(L-N-benzyloxycarbonylvalyl)-2- (R) or (S) -1-hydroxy-n-propyl}pyrrolidine.
NMR(CDCl$_3$)δ: 0.80-2.30 (16H, m), 3.20-4.60 (6H, m), 5.07 (2H, s), 5.60-6.90 (1H, br), 7.30 (5H, s)
The other product which has lower R$_f$ value, L-1-(L-N-benzyloxycarbonylvalyl)-2-{(S) or (R) -1-hydroxy-n-propyl}pyrrolidine.
NMR(CDCl$_3$)δ: 0.80-2.30 (16H, m), 3.20-4.50 (6H, m), 5.08 (2H, s), 5.50-5.80 (1H, br), 7.33 (5H, s)

EXAMPLE 2

Preparation of L-1-(L-N-benzyloxycarbonylvalyl)-2-{(R) or (S)-1-hydroxyethyl}pyrrolidine In the same manner as in Example 1, a mixture of L-2-{(R) or (S)-1-hydroxyethyl}pyrrolidine (0.6 g, 4.8 mmol) which was prepared in Reference Example 2, L-N-benzyloxycarbonylvaline (1.20 g, 4.8 mmol), HOBt (0.65 g, 4.8 mmol), triethylamine (1 ml), and WSC (0.92 g, 4.8 mmol) was stirred for 2 hours at −10° C.~−20° C. and overnight at room temperature to give L-1-(L-N-benzyloxycarbonylvalyl)-2-{(R) or (S)-1-hydroxyethyl}pyrrolidine.
NMR(CDCl$_3$)δ: 0.80-1.35 (9H, m), 1.35-0.20 (5H, m), 3.15-4.60 (5H, m), 5.07 (2H, s), 5.40-5.80 (2H, br), 7.33 (5H, s)

EXAMPLE 3

Preparation of L-1-(L-N-benzyloxycarbonylvalyl)-2-{(S) or (R)-1-hydroxyethyl}pyrrolidine In the same manner as in Example 1, a mixture of L-2-{(S) or (R)-1-hydroxyethyl}pyrrolidine (0.60 g, 4.8 mmol) which was prepared in Reference Example 3, L-N-benzyloxycarbonylvaline (1.20 g, 4.8 mmol), HOBt (0.65 g, 4.8 mmol), triethylamine (1 ml), and WSC (0.92 g, 4.8 mmol) was stirred for 2 hours at −10° C.~−20° C. and overnight at room temperature to give L-1-(L-N-benzyloxycarbonylvalyl)-2-{(S) or (R)-1-hydroxyethyl}pyrrolidine.
NMR(CDCl$_3$)δ: 0.80-1.35 (9H, m), 1.40-2.30 (5H, m), 3.20-4.90 (6H, m), 5.07 (2H, s), 6.03 (1H, d, J=10 Hz), 7.32 (5H, s)

EXAMPLE 4

Preparation of L-1-benzoyl-2-{(R,S)-1-hydroxy-n-propyl}pyrrolidine

In the same manner as in Example 1, a mixture of L-2-{(R,S)-1-hydroxy-n-propyl}pyrrolidine (1.25 g, 8.9 mmol), benzoic acid (1.10 g, 8.9 mmol), triethylamine (1 ml), HOBt (1.20 g, 8.9 mmol), and WSC (1.70 g, 8.9 mmol) was stirred for 2 hours at −10° C.~−20° C. and overnight at room temperature to give L-1-benzoyl-2-{(R,S)-1-hydroxy-n-propyl}pyrrolidine
NMR(CDCl$_3$)δ: 1.05 (3H, t, J=6 Hz), 1.20-2.25 (6H, m), 3.40-3.70 (2H, m), 4.00-4.60 (2H, m), 7.43 (5H, s)

EXAMPLE 5

Preparation of L-1-(3-benzoylpropionyl)-2-{(R,S)-1-hydroxy-n-propyl}pyrrolidine

In the same manner as in Example 1, a mixture of L-2-{(R,S)-1-hydroxy-n-propyl}pyrrolidine (1.25 g, 8.9 mmol), 3-benzoylpropionic acid (1.60 g, 8.9 mmol), HOBt (1.20 g, 8.9 mmol), triethylamine (1 ml), and WSC (1.70 g, 8.9 mmol) was stirred for 2 hours at −10° C.∼−20° C. and overnight at room temperature to give L-1-(3-benzoylpropionyl)-2-{(R,S)-1-hydroxy-n-propyl}-pyrrolidine.

NMR(CDCl₃)δ: 1.00 (3H, t, J=6 Hz), 1.50–1.80 (2H, m), 1.80–2.20 (4H, m), 2.60–2.90 (2H, m), 3.30–3.80 (5H, m), 4.00–4.30 (1H, m), 4.73 (1H, d, J=5 Hz), 7.30–7.70 (3H, m), 7.95–8.10 (2H, m)

EXAMPLE 6

Preparation of L-1-(L-N-benzyloxycarbonylvalyl)-2-{(R) or (S)-1-hydroxy-2-methylpropyl}pyrrolidine In the same manner as in Example 1, a mixture of L-2-{(R) or (S)-1-hydroxy-2-methylpropyl}pyrrolidine (1.00 g, 7.0 mmol) which was prepared in Reference Example 5, L-N-benzyloxycarbonylvaline (1.74 g, 7.0 mmol), HOBt (1.00 g, 7.0 mmol), triethylamine (1 ml), and WSC (1.40 g, 7.0 mmol) was stirred for 2 hours at −10° C.∼−20° C. and overnight at room temperature to give L-1-(L-N-benzyloxycarbonylvalyl)-2-{(R) or (S)-1-hydroxy-2-methylpropyl}pyrrolidine.

NMR(CDCl₃) δ: 0.87–1.20 (9H, m), 1.40–2.27 (6H, m), 3.20–4.13 (3H, m), 4.13–4.57 (3H, m), 5.12 (2H, s), 5.40–5.67 (1H, m), 7.37 (5H, s)

EXAMPLE 7

Preparation of L-1-(L-N-benzyloxycarbonylvalyl)-2-{(S) or (R)-1-hydroxy-2-methylpropyl}pyrrolidine In the same manner as in Example 1, a mixture of L-2-{(S) or (R)-1-hydroxy-2-methylpropyl}pyrrolidine (0.50 g, 3.5 mmol) which was prepared in Example 1, L-N-benzyloxycarbonylvaline (0.87 g, 3.5 mmol), HOBt (0.50 g, 3.5 mmol), triethylamine (1 ml), and WSC (0.70 g, 3.5 mmol) was stirred for 2 hours at −10° C.∼−20° C. and overnight at room temperature to give L-1-(L-N-benzyloxycarbonylvalyl)-2-{(S) or (R)-1-hydroxy-2-methylpropyl}pyrrolidine.

NMR(CDCl₃)δ: 0.77–1.20 (9H, m), 1.40–2.60 (6H, m), 3.23–4.00 (3H, m), 4.20–4.67 (3H, m), 5.10 (2H, s), 5.50–5.90 (1H, m), 7.33 (5H, s)

EXAMPLE 8

Preparation of L-1-(L-N-benzyloxycarbonylvalyl)-2-{(R,S)-1-hydroxy-n-butyl}pyrrolidine In the same manner as in Example 1, a mixture of L-2-{(R,S)-1-hydroxy-n-butyl}pyrrolidine (1.00 g, 7.0 mmol), L-N-benzyloxycarbonylvaline (1.75 g, 7.0 mmol), HOBt (0.94 g, 7.0 mmol), triethylamine (1 ml), and WSC (1.34 g, 7.0 mmol) was stirred for 2 hours at −10° C.∼−20° C. and overnight at room temperature to give L-1-(L-N-benzyloxycarbonylvalyl)-2-{(R,S)-1-hydroxy-n-butyl}pyrrolidine.

NMR(CDCl₃)δ: 0.85–2.15 (5H, m), 1.20–1.70 (4H, m), 1.70–2.15 (5H, m), 3.30–4.00 (4H, m), 4.00–4.60 (2H, m), 5.09 (2H, s), 5.57 (1H, br), 7.35 (5H, s)

EXAMPLE 9

Preparation of L-1-(L-N-benzyloxycarbonylvalyl)-2-{(R,S)-1-hydroxy-1-phenylmethyl}pyrrolidine In the same manner as in Example 1, a mixture of L-2-{(R,S)-1-hydroxy-1-phenylmethyl}pyrrolidine (0.85 g, 4.8 mmol), L-N-benzyloxycarbonylvaline (1.20 g, 4.8 mmol), HOBt (0.65 g, 4.8 mmol), triethylamine (0.7 ml), and WSC (0.92 g, 4.8 mmol) was stirred for 2 hours at −10° C.∼−20° C. and overnight at room temperature to give L-1-(L-N-benzyloxycarbonyl-valyl)-2-{(R,S)-1-hydroxy-1-phenylmethyl}pyrrolidine.

NMR(CDCl₃)δ: 1.04 (6H, t, J=6 Hz), 1.40–2.20 (5H, m), 3.40–4.00 (2H, m), 4.20–4.60 (2H, m), 5.08 (2H, s), 5.57 (1H, d, J=9 Hz), 7.33 (10H, s)

EXAMPLE 10

Preparation of L-1-(L-N-benzyloxycarbonylpropyl)-2-{(R,S)-1-hydroxy-n-propyl}pyrrolidine In the same manner as in Example 1, a mixture of L-2-{(R,S)-1-hydroxy-n-propyl}pyrrolidine (1.00 g, 7.2 mmol), L-N-benzyloxycarbonylproline (1.80 g, 7.2 mmol), HOBt (1.00 g, 7.2 mmol), triethylamine (1 ml), and WSC (1.40 g, 7.2 mmol) was stirred for 2 hours at −10° C.∼−20° C. and overnight at room temperature to give L-1-(L-N-benzyloxycarbonylpropyl)-2-{(R,S)-1-hydroxy-npropyl}pyrrolidine.

NMR(CDCl₃)δ: 0.80–2.43 (13H, m), 3.17–4.77 (8H, m), 4.80–5.27 (2H, m), 7.33 (5H, s)

EXAMPLE 11

Preparation of L-1-(L-N-benzyloxycarbonylisoleucyl)-2-{(R,S)-1-hydroxy-n-propyl}pyrrolidine In the same manner as in Example 1, a mixture of L-2-{(R,S)-1-hydroxy-n-propyl}pyrrolidine (1.00 g, 7.2 mmol), L-N-benzyloxycarbonylisoleucine (1.90 g, 7.2 mmol), HOBt (1.00 g, 7.2 mmol), triethylamine (1 ml), and WSC (1.40 g, 7.2 mmol) was stirred for 2 hours at −10° C.∼−20° C. and overnight at room temperature to give L-1-(L-N-benzyloxycarbonylisoleucyl)-2-{(R,S)-1-hydroxy-n-propyl}pyrrolidine.

NMR(CDCl₃)δ: 0.80–2.20 (14H, m), 3.27–3.67 (2H, m), 3.67–4.07 (1H, m), 4.07–4.57 (2H, m), 5.07 (2H, s), 5.63 (1H, d, J=9 Hz), 7.33 (5H, s)

EXAMPLE 12

Preparation of L-1-(L-N-benzyloxycarbonylphenylalanyl)-2-{(R,S)-1-hydroxy-n-propyl}pyrrolidine In the same manner as in Example 1, a mixture of L-2-{(R,S)-1-hydroxy-n-propyl}pyrrolidine (1.00 g, 7.2 mmol), L-N-benzyloxycarbonylphenylalanine (2.20 g, 7.2 mmol), HOBt (1.00 g, 7.2 mmol), triethylamine (1 ml), and WSC (1.40 g, 7.2 mmol) was stirred for 2 hours at −10° C.∼−20° C. and overnight at room temperature to give L-1-(L-N-benzyloxycarbonyl-phenylalanyl)-2-{(R,S)-1-hydroxy-n-propyl}pyrrolidine.

NMR(CDCl₃)δ: 0.80–1.90 (9H, m), 2.50–3.90 (5H, m), 3.93–4.57 (1H, m), 4.57–4.97 (1H, m), 5.07 (2H, s), 5.80 (1H, d, J=9 Hz), 7.30 (5H, s), 7.35 (5H, s)

EXAMPLE 13

Preparation of L-1-(3-benzoylpropionyl)-2-{(R) or (S)-1-hydroxy-2-methylpropyl}pyrrolidine In the same manner as in Example 1, a mixture of L-2-{(R) or (S)-1-hydroxy-2-methylpropyl}pyrrolidine (1.00 g, 7.0 mmol), which was prepared in Reference Example 5, 3-benzoylpropionic acid (1.24 g, 7.0 mmol), HOBt (1.00 g, 7.0 mmol), triethylamine (1 ml), and WSC (1.40 g, 7.0 mmol) was stirred for 2 hours at −10° C.~ −20° C. and overnight at room temperature to give L-1-(3-benzoylpropionyl)-2-{(R) or (S)-1-hydroxy-2-methylpropyl}pyrrolidine NMR(CDCl$_3$)δ: 0.67–1.30 (6H, m), 1.40–2.23 (5H, m), 2.40–2.93 (2H, m), 2.93–3.90 (4H, m), 4.10–4.40 (1H, m), 4.75 (1H, d, J=5 Hz), 7.20–7.77 (3H, m), 7.93–8.27 (2H, m)

EXAMPLE 14

Preparation of L-1-(3-benzoylpropionyl)-2-{(S) or (R)-1-hydroxy-2-methylpropyl}pyrrolidine In the same manner as in Example 1, a mixture of L-2-{(S) or (R)-1-hydroxy-2-methylpropyl}pyrrolidine (1.00 g, 7.0 mmol) which was prepared in Reference Example 6, 3-benzoylpropionic acid (1.24 g, 7.0 mmol), HOBt (1.00 g, 7.0 mmol), triethylamine (1 ml), and WSC (1.40 g, 7.0 mmol) was stirred for 2 hours at −10° C.~ −20° C. and overnight at room temperature to give L-1(3-benzoylpropionyl)-2-{(S) or (R)-1-hydroxy-2-methylpropyl}pyrrolidine.

NMR(CDCl$_3$)δ: 0.73–1.15 (6H, m), 1.43–2.43 (5H, m), 2.43–3.00 (2H, m), 3.20–4.00 (4H, m), 4.00–4.70 (2H, m), 7.27–7.67 (3H, m), 7.90–8.15 (2H, m)

EXAMPLE 15

Preparation of L-1-(3-benzoylpropionyl)-2-{(R,S)-1-hydroxy-n-butyl}pyrrolidine

In the same manner as in Example 1, a mixture of L-2-{(R,S)-1-hydroxy-n-butyl}pyrrolidine (1.15 g, 8.0 mmol), 3-benzoylpropionic acid (1.43 g, 8.0 mmol), HOBt (1.10 g, 8.0 mmol), triethylamine (1 ml), and WSC (1.53 g, 8.0 mmol) was stirred for 2 hours at −10° C.~ −20° C. and overnight at room temperature to give L-1(3-benzoylpropionyl)-2-{(R,S)-1-hydroxy-n-butyl}pyrrolidine.

NMR(CDCl$_3$)δ: 0.70–2.33 (11H, m), 2.50–2.93 (2H, m), 3.00–4.33 (7H, m), 7.30–7.73 (3H, m), 7.80–8.20 (2H, m)

EXAMPLE 16

Preparation of L-1-(3-benzoylpropionyl)-2-{(R) or (S)-1-hydroxy-1-pehnylmethyl}pyrrolidine In the same manner as in Example 1, a mixture of L-2-{(R,S)-1-hydroxy-1-phenylmethyl}pyrrolidine (0.85 g, 4.8 mmol), 3-benzoylpropionic acid (0.85 g, 4.8 mmol), HOBt (0.65 g, 4.8 mmol), triethylamine (1 ml), and WSC (0.92 g, 4.8 mmol) was stirred for 2 hours at −10° C.~ −20° C. and overnight at room temperature to give two products which have different R$_f$ value each other.

The NMR spectra data of the two products were showed. One product which has higher R$_f$ value, L-1-(3-benzoylpropionyl)-2-{(R) or (S)-1-hydroxy-1-phenylmethyl}pyrrolidine.

NMR(CDCl$_3$)δ: 1.40–2.20 (4H, m), 2.72 (2H, t, J=6 Hz), 3.00–3.70 (4H, m), 4.52 (1H, m), 5.00 (1H, d, J=3 Hz), 5.87 (1H, br), 7.15–7.65 (8H, m), 7.80–8.20 (2H, m)

The other product which has lower R$_f$ value, L-1-(3-benzoylpropionyl)-2-{(S) or (R)-1-hydroxy-1-phenylmethyl}pyrrolidine.

NMR(CDCl$_3$)δ: 1.50–2.10 (4H, m), 2.70–2.90 (2H, m), 3.30–3.80 (4H, m), 4.60–4.70 (2H, m), 5.45 (1H, br), 7.20–7.60 (8H, m), 7.90–8.10 (2H, m)

EXAMPLE 17

Preparation of L-1-benzoyl-2-(2-methylthio-2-methylsulfoxyacetyl)-pyrrolidine

To a suspension of sodiuum hydride (60% oil dispersion, 0.52 g, 13 mmol) in 1,2-dimethoxyethane (15 ml) was added methyl methylsulfinylmethyl sulfide (1.60 g, 13 mmol), followed by stirring for 2 hours at 50° C.–55° C. Methyl L-1-benzoylprolinate (1.00 g, 4.3 mmol) which was prepared in Reference Example 9 was added to the reaction mixture with ice-cooling, followed by stirring overnight at room temperature. The reaction mixture was poured into ice water and extracted with ethyl acetate. The extract was dried over anhydrous magnesium sulfate. Evaporation of ethyl acetate gave L-1-benzoyl-2-(2-methylthio-2-methylsulfoxyacetyl)-pyrrolidine.

NMR(CDCl$_3$)δ: 1.70–2.65 (4H, m), 2.22 (3H, s), 2.84 (3H, s), 3.45–3.85 (2H, m), 4.74 (1H, s), 4.75–5.00 (1H, m), 7.30–7.70 (5H, m)

EXAMPLE 18

Preparation of ethyl 2-oxo-2-(L-1-benzoylpyrrolidine-2-yl)acetate

A mixture of L-1-benzoyl-2-(2-methylthio-2-methylsulfoxyacetyl)pyrrolidine (7.00 g, 21.5 mmol) and cupric chloride dihydrate (3.67 g, 21.5 mmol) in ethanol (100 ml) was stirred overnight at room temperature. After removal of ethanol by distillation, the residue was dissolved in ethyl acetate and the solution was washed with water, dried over anhydrous magnesium sulfate. Evaporation of the solvent gave an oil, which was subject to column chromatography on silica gel. Elution with ethyl acetate gave ethyl 2-oxo-2-(L-1-benzoylpyrrolidin-2-yl)acetate.

NMR(CDCl$_3$)δ: 1.37 (3H, t, J=7 Hz), 1.70–2.70 (4H, m), 3.50–3.93 (2H, m), 4.35 (2H, q, J=7 Hz), 5.10–5.40 (1H, m), 7.30–7.70 (5H, m)

EXAMPLE 19

Preparation of ethyl (R,S)-2-hydroxy-2-(L-1-benzoylpyrrolidin-2-yl)acetate

To a methanol (30 ml) solution of ethyl 2-oxo-2-(L-1-benzoylpyrrolidin-2-yl)acetate was added gradually sodium borohydrate (13 mg) under ice-cooling, followed by stirring for one hour at room temperature. After removal of methanol by distillation, the residue was dissolved in ethyl acetate and the solvent was washed with a saturated aqueous sodium chloride solution dried over anhydrous magnesium sulfate. Evaporation of ethyl acetate gave an oil, which was subjected to column chromatography on silica gel. Elution with ethyl acetate gave ethyl (R,S)-2-hydroxy-2-(L-1-benzoylpyrrolidin-2-yl)acetate.

NMR(CDCl$_3$)δ: 1.35 (3H, t, J=7 Hz), 1.80–2.40 (4H, m), 3.40–3.95 (3H, m), 4.10–4.50 (3H, m), 4.60–4.80 (1H, m), 7.43 (5H, s)

EXAMPLE 20

Preparation of ethyl (R,S)-2-hydroxy-2-{L-1-(L-N-benzyloxycarbonylvalyl)pyrrolidin-2-yl}acetate To a mixture of L-N-benzyloxycarbonylvaline (2.25 g, 9.0 mmol), ethyl (R,S)-2-hydroxy-2-(L-pyrrolidin2-yl)acetate hydrochloride (1.88 g, 9.0 mmol) which was prepared in Reference Example 10, and HOBt (1.21 g, 9.0 mmol) in chloroform (40 ml) were added triethylamine (3 ml) and WSC (1.72 g, 9.0 mmol) under carbon tetrachloride-dry ice cooling, followed by stirring for 2 hours at the same temperature and overnight at room temperature. The reaction mixture was poured into an aqueous sodium hydrogen carbonate solution and extracted with chloroform. The extract was washed with water, dried over anhydrous magnesium sulfate. Evaporation of chloroform to give an oil, which was subjected to column chromatography on silica gel. Elution with n-hexane: ethyl acetate=1:1 gave ethyl (R,S)-2-hydroxy-2-{L-1-(L-N-benzyloxycarbonylvalyl)pyrrolidin-2-yl}acetate.

NMR(CDCl$_3$)δ:0.97 (6H, t, J=7 Hz), 1.30 (3H, t, J=8 Hz), 1.60–2.30 (5H, m), 3.30–3.95 (3H, m), 4.10–4.60 (4H, m), 4.72 (1H, d, J=2 Hz), 5.08 (2H, s), 5.37–5.70 (1H, br), 7.35 (5H, s)

EXAMPLE 21

Preparation of ethyl (R,S)-2-hydroxy-2-(L-1{L-N-benzyloxycarbonylisoleucyl)pyrrolidin-2-yl}acetate In the same manner as in Example 20, a mixture of ethyl (R,S)-2-hydroxy-2-(L-pyrrolidin-2yl)acetate hydrochloride (1.00 g, 4.8 mmol) which was prepared in Reference Example 10, L-N-benzyloxycarbonylisoleucine (1.28 g, 4.8 mmol), WSC (0.93 g, 4.8 mmol), HOBt (0.65 g 4.8 mmol), and triethylamine (1.7 ml) was stirred for 2 hours at −10° C.∼−20° C. and overnight at room temperature gave ethyl (R,S)-2-hydroxy-2-{L-1-(L-N-benzyloxycarbonylisoleucyl)pyrrolidin-2-yl}-acetate.

NMR(CDCl$_3$)δ: 0.96 (6H, t, J=5 Hz), 1.31 (3H, t, d, J=7 Hz, J=3 Hz), 1.45–2.30 (7H, m), 3.10–4.00 (3H, m), 4.10–4.60 (4H, m), 4.75 (1H, d, J=2 Hz), 5.08 (2H, s), 5.40–5.70 (1H, br), 7.34 (5H, s)

EXAMPLE 22

Preparation of ethyl (R,S)-2-hydroxy-2{L-1-(L-N-benzyloxycarbonylpropyl)pyrrolidin-2-yl}acetate In the same manner as in Example 20, a mixture of ethyl (R,S)-2-hydroxy-2-(L-pyrrolidin-2-yl)acetate hydrochloride (1.00 g, 4.8 mmol) which was prepared in Reference Example 10, L-N-benzyloxycarbonylproline (1.20 g, 4.8 mmol), WSC (0.93 g, 4.8 mmol), HOBt (0.65 g, 4.8 mmol), and triethylamine (1.7 ml) was stirred for 2 hours at −10° C.∼−20° C. and overnight at room temperature gave ethyl (R,S)-2-hydroxy-2-{L-1-(L-N-benzyloxycarbonylprolyl)pyrrolidin-2yl}acetate.

NMR(CDCl$_3$)δ: 1.25 (3H, t, J=7 Hz), 1.70–2.30 (8H, m), 3.30–3.90 (4H, m), 3.90–4.90 (6H, m), 5.10 (2H, d, J=3 Hz), 7.32 (5H, s)

EXAMPLE 23

Preparation of ethyl 2-oxo-2-{ L-1-(L-N-benzyloxycarbonylvalyl)pyrrolidin-2-yl}acetate To a dichloromethane (5 ml) solution of oxalyl chloride (1.02 g, 8.0 mmol) was added dropwise a dichloromethane (5 ml) solution of DMSO (1.26 g, 16.0 mmol) at −50° C.∼−60° C. After 2 minutes, a dichloromethane (10 ml) solution of ethyl (R,S)-2-hydroxy-2-{L-1-(L-N-benzyloxycarbonylvalyl)pyrrolidin-2-yl}acetate (1.64 g, 4.0 mmol) was added dropwise to the reaction mixture at −50° C.∼−60° C. After 15 minutes, triethylamine (4.04 g, 40.0 mmol) was added dropwise to the reaction mixture for 5 minutes at the same temperature, followed by stirring for one hour at room temperature. The reaction mixture was poured into water and extracted twice with dichloromethane. After removal of dichloromethane by distillation, the residue was dissolved in ether and the solvent was washed successively with a cold 1% hydrochloric acid, a saturated aqueous sodium chloride solution, dried over anhydrous magnesium sulfate. Evaporation of ether gave ethyl 2-oxo-2(L-1-{L-N-benzyloxycarbonylvalyl)pyrrolidin-2-yl}acetate.

NMR(CDCl$_3$)δ: 0.97 (6H, t, J=7 Hz), 1.36 (3H, t, J=8 Hz), 1.65–2.45 (5H, m), 3.48–3.98 (2H, m), 4.20–4.45 (3H, m), 4.90–5.26 (3H, m), 5.27–5.67 (1H, br), 7.33 (5H, s)

EXAMPLE 24

Preparation of ethyl 2-oxo-2-{L-1-(L-N-benzyloxycarbonylisoleucyl)pyrrolidin-2-yl}acetate In the same manner as in Example 23, ethyl (R,S)-2-hydroxy-2-{L-1-(L-N-benzyloxycarbonylisoleucyl)-pyrrolidin-2-yl}acetate (0.5 g, 1.2 mmol) was oxidized to ethyl 2-oxo-2-{L-1-(L-N-benzyloxycarbonylisoleucyl)pyrrolidin-2-yl}acetate by oxalyl chloride (0.14 g, 1.4 mmol), DMSO (0.22 g, 2.8 mmol), and triethylamine (0.71 g, 7.0 mmol) in dichloromethane.

NMR(CDCl$_3$)δ: 0.94 (6H, t, J=6 Hz), 1.34 (3H, t, J=7 Hz), 1.50–2.30 (7H, m), 3.40–4.00 (2H, m), 4.10–4.50 (3H, m), 4.90–5.20 (3H, m), 5.60 (1H, d, J=9 Hz), 7.30 (5H, s)

EXAMPLE 25

Preparation of ethyl 2-oxo-2-{L-1-(L-N-benzyloxycarbonylpropyl)pyrrolidin-2-yl}acetate In the same manner as in Example 23, ethyl (R,S)-2-hydroxy-2-{L-1-(L-N-benzyloxycarbonylprolyl)pyrrolidin-2-yl}acetate (0.60 g, 1.5 mmol) was oxidized to ethyl 2-oxo-2-{L-1-(L-N-benzyloxycarbonylprolyl)pyrrolidin-2-yl}acetate by oxalyl chloride (0.44 g, 3.4 mmol), DMSO (0.55 g, 7.0 mmol), and triethylamine (1.77 g, 17.5 mmol) in dichloromethane.

NMR(CDCl$_3$)δ: 1.37 (3H, t, J=7 Hz), 1.70–2.50 (8H, m), 3.30–4.00 (4H, m), 4.15–4.70 (3H, m), 4.80–5.30 (3H, m), 7.43 (5H, s)

EXAMPLE 26

Preparation of L-1-(L-N-benzyloxycarbonylvalyl)-2-(1,3-dioxolan-2-yl)pyrrolidine To a mixture of L-(1,3-dioxolan-2-yl)pyrrolidine (1.48 g, 10.3 mmol) which was prepared in Reference Example 12, L-N-benzyloxycarbonylvaline (2.60 g, 10.3 mmol), and HOBt (1.50 g, 10.3 mmol) in chloroform under carbon tetrachloride-dry ice cooling were added triethylamine (2 ml) and WSC (2.00 g, 10.3 mmol), followed by stirring for 2 hours at the same temperature and overnight at room temperature. The reaction mixture was poured into an aqueous sodium hydrogen carbonate solution and extracted with chloroform. The extract was washed with a saturated aqueous sodium chloride solution and dried over anhydrous magnesium sulfate. Evaporation of chloroform gave an oil, which was subjected to column chromatography on silica gel.

Elution with ethyl acetate gave L-1-(L-N-benzyloxycarbonylvalyl)-2-(1,3-dioxolan-2-yl)pyrrolidine.
NMR(CDCl₃)δ: 0.93 (3H, d, J=6 Hz), 1.00 (3H, d, J=6 Hz), 1.50–2.33 (5H, m), 3.50–5.00 (8H, m), 5.07 (2H, s), 5.07–5.20 (1H, m), 5.33–5.75 (1H, m), 7.33 (5H, s)

EXAMPLE 27

Preparation of L-1-(L-N-benzyloxycarbonylprolyl)-2-(1,3-dioxolan-2-yl)pyrrolidine In the same manner as in Example 26, a mixture of L-(1,3-dioxolan-2-yl)pyrrolidine (1.48 g, 10.3 mmol), L-N-benzyloxycarbonylproline (2.57 g, 10.3 mmol), HOBt (1.50 g, 10.3 mmol), WSC (2.00 g, 10.3 mmol), and triethylamine (2 ml) was stirred for 2 hours at −10° C.~−20° C. and overnight at room temperature gave L-1-(L-N-benzyloxycarbonylprolyl)-2-(1,3-dioxolan-2-yl)pyrrolidine.
NMR(CDCl₃)δ: 1.40–2.40 (8H, m), 3.23–4.17 (8H, m), 4.20–5.33 (5H, m), 7.33 (5H, s)

EXAMPLE 28

Preparation of ethyl (R,S)-2-hydroxy-2-{L-1-(4-methoxybenzoyl)pyrrolidin-2-yl}acetate In the same manner as in Example 20, a mixture of 4-methoxybenzoic acid (1.05 g, 6.9 mmol), ethyl (R,S)-2-hydroxy-2-(L-pyrrolidin-2-yl)acetate hydrochloride (1.44 g, 6.9 mmol), WSC (1.32 g, 6.9 mmol), HOBt (0.93 g, 6.9 mmol), and triethylamine (2.4 ml) was stirred for 2 hours at −10° C.~−20° C. and overnight at room temperature gave ethyl (R,S)-2-hydroxy-2-{L-1-(4-methxybenzoyl)pyrrolidin-2-yl}acetate.
NMR(CDCl₃)δ: 1.29 (3H, t, J=7 Hz), 1.63–1.79 (1H, m), 1.90–2.10 (3H, m), 3.46–3.57 (2H, m), 3.84 (3H, s), 4.25 (2H, q, J=7 Hz), 4.49 (1H, d, J=8 Hz), 4.60 (1H, t, J=8 Hz), 4.70 (1H, d, J=7 Hz), 6.89–6.92 (2H, m), 7.49–7.53 (2H, m)

EXAMPLE 29

Preparation of ethyl (R,S)-2-hydroxy-2-{L-1-(3,4-dimethoxybenzoyl)pyrrolidin-2-yl}acetate In the same manner as in Example 20, a mixture of 3,4-dimethoxybenzoic acid (1.26 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at −10° C.~−20° C. and overnight at room temperature gave ethyl (R,S)-2-hydroxy-2-{L-1-(3,4-dimethoxybenzoyl)pyrrolidin-2-yl}acetate.
NMR(CDCl₃)δ: 1.30 (3H, t, J=7 Hz), 1.65–1.79 (1H, m), 1.91–2.12 (3H, m), 3.48–3.65 (2H, m), 3.90 (3H, s), 3.92 (3H, s), 4.26 (2H, q, J=7 Hz), 4.42 (1H, d, J=7 Hz), 4,57–4.63 (1H, m), 4.72 (1H, d, J=7 Hz), 6.86 (1H, d, J=9Hz), 7.10–7.13 (2H, m)

EXAMPLE 30

Preparation of ethyl (R,S)-2-hydroxy-2-{L-1-(4-methylbenzoyl)pyrrolidin-2-yl}acetate In the same manner as in Example 20, a mixture of 4-methylbenzoic acid (0.94 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at −10° C.~−20° C. and overnight at room temperature gave ethyl (R,S)-2-hydroxy-2-{L-1-(4-methylbenzoyl)pyrrolidin-2-yl}acetate
NMR(CDCl₃)δ: 1.26–1.38 (3H, m), 1.65–1.75 (1H, m), 1.90–2.20 (3H, m), 2.38 (3H, s), 3.47–3.52 (2H, m), 4.26 (2H, q, J=7 Hz), 4.48 (1H, d, J=7 Hz), 4.59 (1H, t, J=8 Hz), 4.70 (1H, d, J=7 Hz), 7.18–7.22 (2H, m), 7.39–7.44 (2H, m)

EXAMPLE 31

Preparation of ethyl (R,S)-2-hydroxy-2-{L-1-(3,4,5-trimethoxybenzoyl)pyrrolidin-2-yl}acetate In the same manner as in Example 20, a mixture of 3,4,5-trimethoxybenzoic acid (1.46 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at −10° C.~−20° C. and overnight at room temperature gave ethyl (R,S)-2-hydroxy-2-{L-1-(3,4,5-trimethoxybenzoyl)pyrrolidin-2-yl}acetate.
NMR(CDCl₃)δ: 1.34 (3H, t, J=7 Hz), 1.65–1.77 (1H, m), 1.90–2.23 (3H, m), 3.23–3.42 (2H, m), 3.85 (3H, s), 3.87 (3H, s), 3.91 (3H, s), 3.97 (1H, d, J=7 Hz), 4.17–4.38 (3H, m), 4.62–4.68 (1H, m), 6.66 (1H, d, J=9 Hz), 6.96 (1H, d, J=9 Hz)

EXAMPLE 32

Preparation of ethyl (R,S)-2-hydroxy-2-{L-1-(4-fluorobenzoyl)pyrrolidin-2-yl}acetate In the same manner as in Example 20, a mixture of 4-fluorobenzoic acid (0.97 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at −10° C.~−20° C. and overnight at room temperature gave ethyl (R,S)-2-hydroxy-2-{L-1-(4-fluorobenzoyl)pyrrolidin-2-yl}acetate
NMR(CDCl₃)δ: 1.30 (3H, t, J=7 Hz), 1.65–2.15 (4H, m), 3.45–3.52 (2H, m), 4.16 (1H, d, J=7 Hz), 4.27 (2H, q, J=7 Hz), 4.57–4.64 (1H, m), 4.74 (1H, d, J=7 Hz), 7.06–7.12 (2H, m), 7.52–7.57 (2H, m)

EXAMPLE 33

Preparation of ethyl (R,S)-2-hydroxy-2-[L-1-3-(4-n-buthoxybenzoyl)propionyl)pyrrolidin-2-yl]acetate In the same manner as in Example 20, a mixture of 3-(4-n-buthoxybenzoyl)propionic acid (1.73 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at −10° C.~−20° C. and overnight at room temperature gave ethyl (R,S)-2-hydroxy-2-[L-1-{3-(4-n-buthoxybenzoyl)propionyl}pyrrolidin-2-yl]acetate.
NMR(CDCl₃)δ: 0.98 (3H, t, J=8 Hz), 1.27 (3H, t, J=7 Hz), 1.43–1.57 (2H, m), 1.73–2.17 (6H, m), 2.60–2.86 (2H, m), 3.13–3.73 (4H, m), 4.02 (2H, t, J=7 Hz), 4.10–4.30 (2H, m), 4.36–4.46 (2H, m), 4.65–4.63 (1H, m), 6.88–6.94 (2H, m), 7.94–8.00 (2H, m)

EXAMPLE 34

Preparation of ethyl (R,S)-2-hydroxy-2-[L-1-{3-(4-t-butylbenzoyl)propionyl}pyrrolidin-2-yl]acetate In the same manner as in Example 20, a mixture of 3-(4-t-butylbenzoyl)propionic acid (1.21 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at $-10°$ C. $\sim -20°$ C. and overnight at room temperature gave ethyl (R,S)-2-hydroxy-2-[L-1-{3-(4-t-butylbenzoyl)propionyl}pyrrolidin-2-yl]acetate.

NMR(CDCl$_3$)δ: 1.23–1.34 (12H, m), 1.82–2.09 (4H, m), 2.60–2.88 (2H, m), 3.22–3.70 (4H, m), 4.10–4.42 (4H, m), 4.65–4.68 (1H, m) 7.46–7.49 (2H, m), 7.93–7.96 (2H, m)

EXAMPLE 35

Preparation of ethyl (R,S)-2-hydroxy-2-[L-1-{3-(2,5-dimethoxybenzoyl)propionyl}pyrrolidin-2-yl]acetate In the same manner as in Example 20, a mixture of 3-(2,5-dimethoxybenzoyl)propionic acid (1.23 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at $-10°$ C. $\sim -20°$ C. and overnight at room temperature gave ethyl (R,S)-2-hydroxy-2-[L-1-{3-(2,5-dimethoxybenzoyl)propionyl}pyrrolidin-2-yl]acetate.

NMR(CDCl$_3$)δ: 1.26–1.32 (3H, m), 1.80–2.15 (4H, m), 2.56–2.83 (2H, m), 3.26–3.72 (4H, m), 3.79 (3H, s), 3.88 (3H, s), 4.11–4.30 (2H, m), 4.37–4.50 (2H, m), 4.65–4.69 (1H, m), 7.00–7.05 (2H, m), 7.30–7.32 (1H, m)

EXAMPLE 36

Preparation of ethyl 2-oxo-2-{L-1-(4-methoxybenzoyl)pyrrolidin-2-yl}acetate

In the same manner as in Example 23, ethyl (R,S)-2-hydroxy-2-{L-1-(4-methoxybenzoyl)pyrrolidin-2-yl}acetate (0.30 g, 0.98 mmol) was oxidized to ethyl 2-oxo-2-{L-1-(4-methoxybenzoyl)pyrrolidin-2-yl}acetate by oxalyl chloride (0.30 g, 2.4 mmol), DMSO (0.42 g, 5.4 mmol), and triethylamine (1.10 g, 10.9 mmol) in dichloromethane.

NMR(CDCl$_3$)δ: 1.38 (3H, t, J=7 Hz), 1.90–2.07 (3H, m), 3.67–3.73 (2H, m), 3.84 (3H, s), 4.35 (2H, q, J=7 Hz), 5.24 (1H, t, J=8 Hz), 6.90 (2H, d, J=9 Hz), 7.56 (2H, d, J=9 Hz)

EXAMPLE 37

Preparation of ethyl 2-oxo-2-{L-1-(3,4-dimethoxybenzoyl)pyrrolidin-2-yl}acetate

In the same manner as in Example 23, ethyl (R,S)-2-hydroxy-2-{L-1-(3,4-dimethoxybenzoyl)pyrrolidin-2-yl}acetate (0.33 g, 0.98 mmol) was oxidized to ethyl 2-oxo-2-{L-1-(3,4-dimethoxybenzoyl)pyrrolidin-2-yl}acetate by oxalyl chloride (0.30 g, 2.4 mmol), DMSO (0.42 g, 5.4 mmol), and triethylamine (1.10 g, 10.9 mmol) in dichloromethane.

NMR(CDCl$_3$)δ: 1.39 (3H, t, J=7 Hz), 1.96–2.16 (2H, m), 2.31–2.40 (1H, m), 3.70–3.80 (2H, m), 3.89 (3H, s), 2.94 (3H, s), 4.34 (2H, q, J=7 Hz), 5.23–5.30 (1H, m), 6.85 (1H, d, J=8 Hz), 7.10–7.20 (2H, m)

EXAMPLE 38

Preparation of ethyl 2-oxo-2-{L-1-(4-methylbenzoyl)-pyrrolidin-2-yl}acetate

In the same manner as in Example 23, ethyl (R,S-2-hydroxy-2-{L-1-(4-methylbenzoyl)pyrrolidin-2-yl}acetate (0.29 g, 0.98 mmol) was oxidized to ethyl 2-oxo-2-{L-1-(4-methylbenzoyl)pyrrolidin-2-yl}acetate by oxalyl chloride (0.30 g, 2.4 mmol), DMSO (0.42 g, 5.4 mmol), and triethylamine (1.10 g, 10.9 mmol) in dichloromethane.

NMR(CDCl$_3$)δ: 1.39 (3H, t, J=7 Hz), 1.95–2.15 (3H, m), 2.35–2.42 (1H, m), 2.38 (3H, s), 3.60–3.76 (2H, m), 4.35 (2H, q, J=7 Hz), 5.21–5.2 (1H, m), 7.18–7.22 (2H, m), 7.45–7.48 (2H, m)

EXAMPLE 39

Preparation of ethyl 2-oxo-2-{L-1-(3,4,5-trimethoxybenzoyl)pyrrolidin-2-yl}acetate In the same manner as in Example 23, ethyl (R,S)-2-hydroxy-2-{L-1-(3,4,5-trimethoxybenzoyl)pyrrolidin-2-yl}acetate was oxidized to ethyl 2-oxo-2-{L-1-(3,4,5-trimethoxybenzoyl)pyrrolidin-2-yl}acetate by oxalyl chloride (0.30 g, 2.4 mmol), DMSO (0.42 g, 5.4 mmol), and triethylamine (1.10 g, 10.9 mmol) in dichloromethane.

NMR(CDCl$_3$)δ: 1.40 (3H, t, J=7 Hz), 1.90–2.03 (3H, m), 2.30–2.40 (1H, m), 3.37–3.57 (2H, m), 3.88 (3H, s), 3.89 (3H, s), 3.91 (3H, s) 4.37 (2H, q, J=7 Hz), 5.23–5.29 (1H, m), 6.68 (1H, d, J=9 Hz), 7.02 (1H, d, J=9 Hz)

EXAMPLE 40

Preparation of ethyl 2-oxo-2-{L-1-(4-fluorobenzoyl)pyrrolidin-2-yl}acetate

In the same manner as in Example 23, ethyl (R,S)-2-hydroxy-2-{L-1-(4-fluorobenzoyl)pyrrolidin-2-yl}acetate (0.29 g, 0.98 mmol) was oxidized to ethyl 2-oxo-2-{L-1-(4-fluorobenzoyl)pyrrolidin-2-yl}acetate by oxalyl chloride (0.30 g, 2.4 mmol), DMSO (0.42 g, 5.4 mmol), and triethylamine (1.10 g, 10.9 mmol) in dichloromethane.

NMR(CDCl$_3$)δ: 1.39 (3H, t, J=7 Hz), 1.95–2.15 (3H, m) 2.35–2.45 (1H, m), 3.58–3.75 (2H, m), 4.37 (2H, t, J=7 Hz), 5.23–5.28 (1H, m), 7.06–7.13 (2H, m), 7.56–7.61 (2H, m)

EXAMPLE 41

Preparation of ethyl 2-oxo-2-[L-1-{3-(4-n-buthoxybenzoyl)propionyl}pyrrolidin-2-yl]acetate In the same manner as in Example 23, ethyl (R,S)-2-hydroxy-2-[L-1-{3-(4-n-buthoxybenzoyl)propionyl}pyrrolidin-2-yl}acetate was oxidized to ethyl 2-oxo-2-[L-1-{3-(4-n-buthoxybenzoyl)propionyl}pyrrolidin-2-yl]acetate by oxalyl chloride (0.30 g, 2.4 mmol), DMSO (0.42 g, 5.4 mmol), and triethylamine (1.10 g, 10.9 mmol) in dichloromethane.

NMR(CDCl₃)δ: 0.98 (3H, t, J=7 Hz), 1.35 (3H, t, J=7 Hz), 1.50 (2H, q, J=7 Hz), 1.73–1.84 (2H, m), 1.98–2.23 (2H, m), 2.28–2.33 (2H, m), 2.61–2.88 (2H, m), 3.14–3.25 (1H, m), 3.44–3.46 (1H, m), 3.73 (2H, t, J=7 Hz), 4.02 (2H, t, J=7 Hz), 4.32 (2H, q, J=7 Hz), 5.04–5.10 (1H, m), 6.88–6.93 (2H, m), 7.93–7.96 (2H, m)

EXAMPLE 42

Preparation of ethyl 2-oxo-2-[L-1-{3-(4-t-butylbenzoyl)propionyl}pyrrolidin-2-yl]acetate In the same manner as in Example 23, ethyl (R,S)-2-hydroxy-2-[L-1-{3-(4-t-butylbenzoyl)propionyl}pyrrolidin-2-yl]acetate (0.35 g, 0.98 mmol) was oxidized to ethyl 2-oxo-2-[L-1-{3-(4-t-butylbenzoyl)propionyl}pyrrolidin-2-yl]acetate by oxalyl chloride (0.30 g, 2.4 mmol), DMSO (0.42 g, 5.4 mmol), and triethylamine (1.10 g, 10.9 mmol) in dichloromethane.

NMR(CDCl₃)δ: 1.22–1.43 (12H, m), 1.98–2.33 (4H, m), 2.62–2.88 (2H, m), 3.17–3.28 (1H, m), 3.37–3.50 (1H, m), 3.71–3.76 (2H, m), 4.31 (2H, q, J=7 Hz), 5.04–5.09 (1H, m), 7.44–7.48 (2H, m), 7.90–7.95 (2H, m)

EXAMPLE 43

Preparation of ethyl 2-oxo-2-[L-1-{3-(2,5-dimethoxybenzoyl)propionyl}pyrrolidin-2-yl]acetate In the same manner as in Example 23, ethyl (R,S)-2-hydroxy-2-[L-1-{3-(2,5-dimethoxybenzoyl)propionyl}pyrrolidin-2-yl]acetate was oxidized to ethyl 2-oxo-2-[L-1-{3-(2,5-dimethoxybenzoyl)propionyl}pyrrolidin-2-yl]acetate by oxalyl chloride (0.30 g, 2.4 mmol), DMSO (0.42 g, 5.4 mmol), and triethylamine (1.10 g, 10.9 mmol) in dichloromethane.

NMR(CDCl₃)δ: 1.35 (3H, t, J=7 Hz), 1.98–2.33 (4H, m), 2.55–2.85 (2H, m), 3.23–3.50 (4H, m), 3.78 (3H, s), 3.85 (3H, s), 4.32 (2H, q, J=7 Hz), 5.05–5.10 (1H, m), 6.88–7.00 (1H, m), 7.01–7.04 (1H, m), 7.28–7.30 (1H, m)

EXAMPLE 44

Preparation of ethyl (R,S)-2-hydroxy-2-{L-1-(3-benzoylpropionyl)pyrrolidin-2-yl}acetate In the same manner as in Example 20, a mixture of 3-benzoylpropionic acid (0.88 g, 5.0 mmol), ethyl (R,S)-2-hydroxy-2-(L-pyrrolidin-2-yl)acetate hydrochloride (1.04 g, 5.0 mmol) which was prepared in Reference Example 10, WSC (0.96 g, 5.0 mmol), HOBt (0.67 g, 5.0 mmol), and triethylamine (1.25 g) was stirred for 2 hours at −10° C. ~ −20° C. and overnight at room temperature gave ethyl (R,S)-2-hydroxy-2-{L-1-(3-benzoylpropionyl)pyrrolidin-2-yl}acetate.

NMR(CDCl₃)δ: 1.25–1.31 (3H, m), 1.83–2.15 (4H, m), 3.23–3.73 (4H, m), 4.17–4.47 (4H, m), 4.68 (1H, d, J=7 Hz), 7.43–7.60 (3H, m), 7.98–8.03 (2H, m)

EXAMPLE 45

Preparation of ethyl (R,S)-2-hydroxy-2-(L-1-benzoylpyrrolidin-2-yl)acetate

The tittle compound which was prepared in Example 19 was synthesized in the same manner as in Example 20. Benzoic acid (0.61 g, 5.0 mmol), ethyl (R,S)-2-hydroxy-2-(L-pyrrolidin-2-yl)acetate hydrochloride (1.04 g, 5.0 mmol) which was prepared in Reference Example 10, WSC (0.96 g, 5.0 mmol), HOBt (0.67 g, 5.0 mmol), and triethylamine (1.25 g) was stirred for 2 hours at −10° C. ~ −20° C. and over night at room temperature gave ethyl (R,S)-2-hydroxy-2-(L-1-benzoylpyrrolidin-2-yl)acetate.

EXAMPLE 46

Preparation of ethyl (R,S)-2-hydroxy-2{L-1-(4-hydroxybenzoyl)pyrrolidin-2-yl}acetate In the same manner as in Example 20, a mixture of 4-hydroxybenzoic acid (0.95 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at −10° C. ~ −20° C. and overnight at room temperature gave ethyl (R,S)-2-hydroxy-2-{L-1-(4-hydroxybenzoyl)pyrrolidin-2-yl}acetate.

NMR(CDCl₃)δ: 1.25–1.34 (3H, m), 1.60–2.20 (4H, m), 3.53–3.72 (2H, m), 4.21–4.42 (3H, m), 4.60–4.80 (2H, m), 6.65–6.76 (2H, m), 7.31–7.40 (2H, m), 7.70–8.05 (1H, brs)

EXAMPLE 47

Preparation of ethyl (R,S)-2-hydroxy-2-{L-1-(4-benzyloxybenzoyl)pyrrolidin-2-yl}acetate In the same manner as in Example 20, a mixture of 4-benzyloxybenzoic acid (1.08 g, 6.9 mmol), ethyl (R,S)-2-hydroxy-2-(L-pyrrolidin-2-yl)acetate hydrochloride (1.44 g, 6.9 mmol) which was prepared in Reference Example 10, WSC (1.32 g, 6.9 mmol), HOBt (0.93 g, 6.9 mmol), and triethylamine (2.4 ml) was stirred for 2 hours at −10° C. ~ −20° C. and overnight at room temperature gave ethyl (R,S)-2-hydroxy-2-{L-1-(4-benzyloxybenzoyl)pyrrolidin-2yl}acetate.

NMR(CDCl₃)δ: 1.29 (3H, t, J=7 Hz), 1.58–2.11 (4H, m), 3.50–3.55 (2H, m), 4.25 (2H, q, J=7 Hz), 4.45 (1H, d, J=7 Hz), 4.60 (1H, t, J=8 Hz), 4.71 (1H, d, J=7 Hz), 5.10 (2H, s), 6.95–7.00 (2H, m), 7.30–7.54 (7H, m)

EXAMPLE 48

Preparation of ethyl 2-oxo-2-(L-1-benzoylpyrrolidin-2-yl)acetate

The tittle compound which was prepared in Example 18 was synthesized in the same manner as in Example 23. Ethyl (R,S)-2-hydroxy-2-(L-1-benzoylpyrrolidin-2-yl)acetate (0.27 g, 0.98 mmol) was oxidized to ethyl 2-oxo-2-(L-1-benzoylpyrrolidin-2-yl)acetate by oxalyl chloride (0.30 g, 2.4 mmol), DMSO (0.42 g, 5.4 mmol), and triethylamine (1.10 g, 10.9 mmol) in dichloromethane.

EXAMPLE 49

Preparation of ethyl 2-oxo-2-{L-1-(3-benzoylpropionyl)pyrrolidin-2-yl}acetate

In the same manner as in Example 23, ethyl (R,S)-2-hydroxy-2-{L-1-(3-benzoylpropionyl)pyrrolidin-2-yl}acetate (0.30 g, 0.9 mmol) was oxidized to ethyl 2-oxo-2-{L-1-(3-benzoylpropionyl)pyrrolidin-2-yl}acetate by oxalyl chloride (0.30 g, 2.4 mmol), DMSO (0.42 g, 5.4 mmol), and triethylamine (1.10 g, 10.9 mmol) in dichloromethane.

NMR(CDCl₃)δ: 1.35 (3H, t, J=7 Hz), 1.99-2.34 (4H, m), 2.62-2.90 (2H, m), 3.19-3.31 (1H, m), 3.40-3.52 (1H, m), 3.72-3.77 (2H, m), 4.32 (2H, q, J=7 Hz), 5.05-5.10 (1H, m), 7.42-7.58 (3H, m), 7.96-8.00 (2H, m)

EXAMPLE 50

Preparation of ethyl 2-oxo-2-{L-1-(4-benzyloxybenzoyl)pyrrolidin-2-yl}acetate

In the same manner as in Example 23, ethyl (R,S)-2-hydroxy-2-{L-1-(4-benzyloxybenzoyl)pyrrolidin-2-yl}acetate (0.13 g, 0.34 mmol) was oxidized to ethyl 2-oxo-2-{L-1-(4-benzyloxybenzoyl)pyrrolidin-2-yl}acetate by oxalyl chloride (0.10 g, 0.8 mmol), DMSO (0.14 g, 1.8 mmol), and triethylamine (0.36 g, 3.6 mmol) in dichloromethane.

NMR(CDCl₃)δ: 1.38 (3H, t, J=7 Hz), 1.94-2.25 (4H, m), 3.67-3.82 (2H, m), 4.35 (2H, q, J=7 Hz), 5.10 (2H, s), 5.21-5.26 (1H, m), 6.96-7.05 (2H, m), 7.32-7.63 (7H, m)

What is claimed is:

1. A compound of the formula

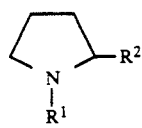

wherein $R^1$ is $C_6H_5CH_2$

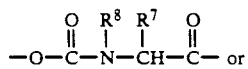

or

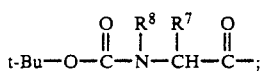

$R^7$ is hydrogen, lower alkyl, benzyl,

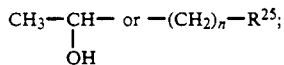

n is an integer from 0 to 4; $R^{25}$ is —OH, —SH, —NH₂, —SCH₃,

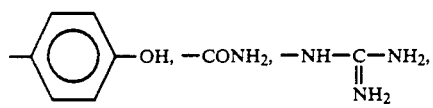

4-imidazolyl, 3-indolyl or —CO₂$R^{26}$; $R^{26}$ is hydrogen, lower alkyl or benzoyl; $R^8$ is hydrogen or, when $R^8$ and $R^7$ are taken together with the adjacent nitrogen atom and carbon atom to which they are attached, they represent pyrrolidine;

$R^2$ is 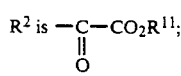

$R^{11}$ is hydrogen, lower alkyl,

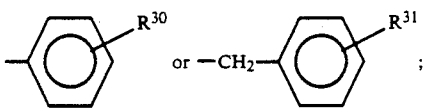

and $R^{30}$ and $R^{31}$ are each independently hydrogen, halogen, lower alkyl or lower alkoxy.

2. A compound according to claim 1, wherein $R^1$ is

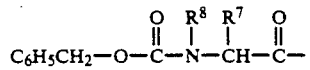

$R^7$ is hydrogen, lower alkyl or benzyl, $R^8$ is hydrogen or, when $R^8$ and $R^7$ are taken together with the adjacent nitrogen atom and carbon atom to which they are attached, they represent pyrrolidine and $R^{11}$ is lower alkyl.

3. A compound of the formula:

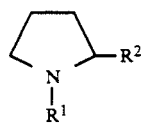

wherein $R^1$ is

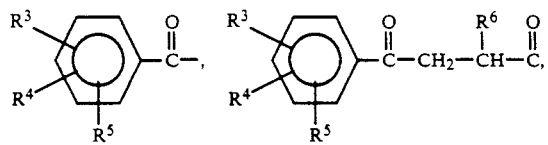

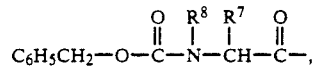

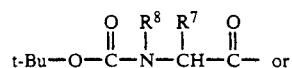

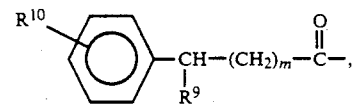

$R^2$ is —CH—CO₂$R^{11}$, —CH—O$R^{12}$ or —CH—$R^{13}$;
       |                |              |
       OH              O$R^{12}$        OH $R^3$, $R^4$ and $R^5$ are each independently hydrogen, hydroxy, halogen, $C_{1-4}$ alkyl, phenyl unsubstituted or substituted with at least one substituent selected from the group consisting of halogen, $C_{1-4}$ alkyl, $C_{1-4}$ alkoxy, —O—$R^{15}$, NH₂, —NH$R^{17}$ and, N—$R^{18}$—$R^{19}$, wherein $R^{15}$ is phenyl; $R^{17}$ is $C_{1-4}$ alkyl; $R^{18}$ and $R^{19}$ are each independently $C_{1-4}$ alkyl, benzyl, $R^6$ is hydrogen or lower alkyl, $R^7$ is hydrogen, lower alkyl, benzyl,

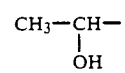

or —(CH₂)ₙ—$R^{25}$ in which n is an integer of 0 to 4 and $R^{25}$ is —OH, —SH, —NH₂, —SCH₃,

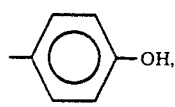

—CONH₂,

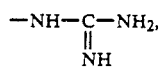

4-imidazolyl, 3-indolyl, or —CO₂R²⁶, in which R²⁶ is hydrogen or C₁₋₄ alkyl; R⁸ is hydrogen or, when R⁸ and R⁷ are taken together with the adjacent nitrogen atom and carbon atom to which they are attached, they represent pyrrolidine; R⁹ is hydrogen, C₁₋₄ alkyl or phenyl; R¹⁰ is hydrogen, C₁₋₄ alkyl, C₁₋₄ alkoxy or halogen; m is an integer of 0 to 3; R¹¹ is hydrogen, C₁₋₄ alkyl, phenyl, or

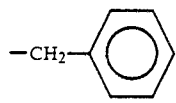

R¹² is lower alkyl or, when R¹² and R¹² are each taken together, they represent lower alkylene; R¹³ is lower alkyl, phenyl, or benzyl.

4. A compound of the formula:

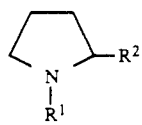

wherein R¹ is

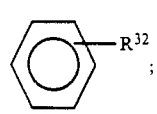

R³, R⁴, and R⁵ are each independently hydrogen, lower alkyl, lower alkoxy, halogen or phenyl; R⁶ is hydrogen or lower alkyl; R⁹ is hydrogen, lower alkyl,

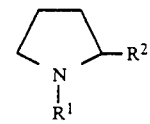

;

R³² is hydrogen, halogen, lower alkyl or lower alkoxy; R¹⁰ is hydrogen, halogen, lower alkyl or lower alkoxy; m is an integer of 0 to 3; R¹¹ is lower alkyl.

5. A compound of the formula:

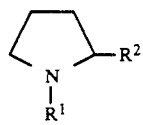

wherein R¹ is

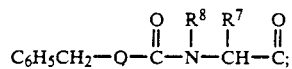

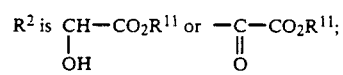

R⁷ is hydrogen, lower alkyl or benzyl; R⁸ is hydrogen or, when R⁸ and R⁷ are taken together with the adjacent nitrogen atom and carbon atom to which they are attached, they represent pyrrolidine; R¹¹ is lower alkyl.

6. A compound of the formula:

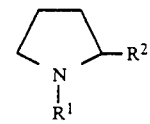

wherein R¹ is C₆H₅CH₂

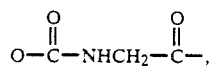

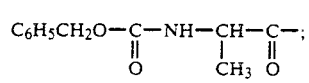

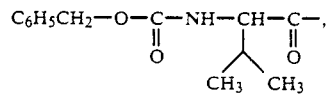

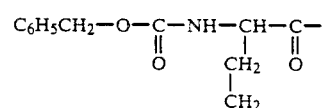

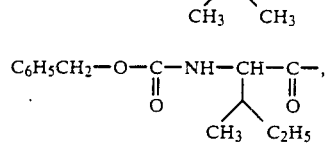

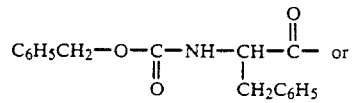

or

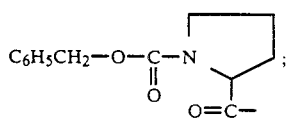

;

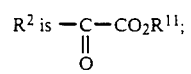

R¹¹ is lower alkyl.

7. A compound of the formula:

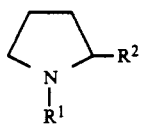

wherein $R^1$ is

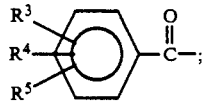

$R^2$ is

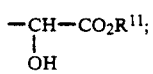

$R^3$, $R^4$ and $R^5$ are each independently hydrogen, lower alkyl, lower alkoxy or halogen; $R^{11}$ is lower alkyl.

8. A compound of the formula:

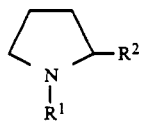

wherein $R^1$ is

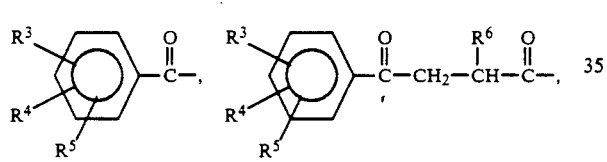

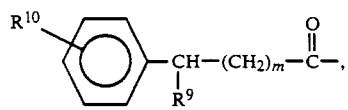

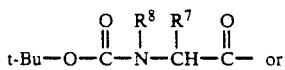

$R^2$ is

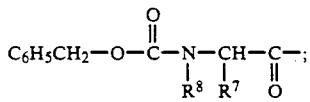

$R^3$, $R^4$ and $R^5$ are each independently hydrogen, lower alkyl, lower alkoxy or halogen; m is an integer 0 to 3; $R^6$ is hydrogen or lower alkyl; $R^9$ is hydrogen, lower alkyl,

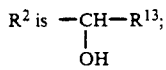

$R^{32}$ is hydrogen, halogen, lower alkyl or lower alkoxy; $R^{10}$ is hydrogen, lower alkyl, lower alkoxy or halogen; $R^7$ is hydrogen, lower alkyl or benzyl; $R^8$ is hydrogen or, when $R^8$ and $R^7$ are taken together with adjacent nitrogen atom and carbon atom to which they are attached they represent pyrrolidine; $R^{13}$ is methyl or ethyl.

9. A compound of the formula:

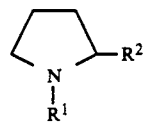

wherein $R^1$ is

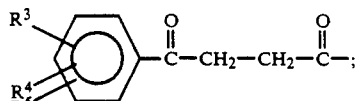

$R^2$ is

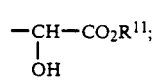

$R^3$, $R^4$ and $R^5$ are each independently hydrogen, lower alkyl, lower alkoxy or halogen; $R^{11}$ is lower alkyl.

10. A compound of the formula:

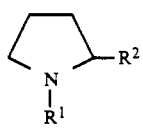

wherein $R^1$ is

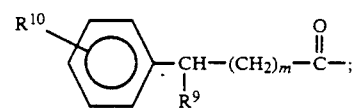

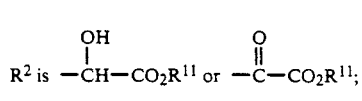

$R^9$ is hydrogen, lower alkyl,

$R^{32}$ is hydrogen, halogen, lower alkyl or lower alkoxy; $R^{10}$ is hydrogen, lower alkyl, lower alkoxy or halogen; m is an integer from 0 to 3; $R^{11}$ is lower alkyl.

11. An anti-amnestic composition comprising a antiamnestically effective amount of a compound according to claim 1 and a pharmaceutically acceptable carrier.

12. A method of treating a patient suffering from, amnesia, comprising administering to the patient a daily dosage of 1 mg to 100 mg/kg of body weight of a compound according to claim 1 one or several times by oral administration or intravenous injection.

* * * * *